(12) United States Patent
Yu et al.

(10) Patent No.: US 10,959,999 B2
(45) Date of Patent: Mar. 30, 2021

(54) SOLID FORMS OF BERBERINE URSODEOXYCHOLATE AND COMPOSITIONS AND METHODS THEREOF

(71) Applicant: SHENZHEN HIGHTIDE BIOPHARMACEUTICAL, LTD., Shenzhen (CN)

(72) Inventors: Meng Yu, Shenzhen (CN); Liping Liu, Manassas, VA (US); Xinxiang Fu, Shenzhen (CN)

(73) Assignee: Shenzhen HighTide Biopharmaceutical, Ltd., Shenzhen (CN)

( * ) Notice: Subject to any disclaimer, the term of this patent is extended or adjusted under 35 U.S.C. 154(b) by 31 days.

(21) Appl. No.: 16/608,457

(22) PCT Filed: May 11, 2018

(86) PCT No.: PCT/CN2018/086461
§ 371 (c)(1),
(2) Date: Oct. 25, 2019

(87) PCT Pub. No.: WO2018/205987
PCT Pub. Date: Nov. 15, 2018

(65) Prior Publication Data
US 2020/0188387 A1    Jun. 18, 2020

(30) Foreign Application Priority Data
May 12, 2017 (CN) .......................... 201710335467.5

(51) Int. Cl.
*A61K 31/4745* (2006.01)
*A61K 45/06* (2006.01)
*C07D 491/147* (2006.01)
*C07J 9/00* (2006.01)

(52) U.S. Cl.
CPC .......... *A61K 31/4745* (2013.01); *A61K 45/06* (2013.01); *C07D 491/147* (2013.01); *C07J 9/00* (2013.01); *C07B 2200/13* (2013.01)

(58) Field of Classification Search
CPC ............... A61K 31/4745; A61K 45/06; C07D 491/147; C07J 9/00; C07B 2200/13
See application file for complete search history.

(56) References Cited

FOREIGN PATENT DOCUMENTS

| CN | 105693805 A | 2/2016 |
|---|---|---|
| CN | 106687460 A | 5/2017 |

OTHER PUBLICATIONS

CN 201710335467.5, First Office Action, Jun. 25, 2019.
CN 201710335467.5, Second Office Action, Nov. 22, 2019.

*Primary Examiner* — John Mabry
(74) *Attorney, Agent, or Firm* — Milstein Zhang & Wu LLC

(57) ABSTRACT

The invention generally relates to solid forms of berberine ursodeoxycholate, and to pharmaceutical compositions, and methods of preparation and therapeutic use thereof. In particular, the invention relates to solid forms of berberine ursodeoxycholate and pharmaceutical compositions thereof useful in treating and/or preventing various diseases or disorders, including metabolic disorders, heart diseases, neurodegenerative diseases and liver diseases.

15 Claims, 26 Drawing Sheets

SOLID FORMS OF BERBERINE URSODEOXYCHOLATE AND COMPOSITIONS AND METHODS THEREOF

PRIORITY CLAIMS AND RELATED APPLICATIONS

This application is the U.S. national phase of and claims priority to PCT/CN2018/086461, filed May 11, 2018, which claims the benefit of priority to Chinese Application No. 201710335467.5, filed May 12, 2017, the content of each of which is incorporated herein by reference in its entirety.

TECHNICAL FIELD OF THE INVENTION

The invention generally relates to solid forms of berberine ursodeoxycholate, and to pharmaceutical compositions and methods of preparation and therapeutic uses thereof. In particular, the invention relates to solid forms (e.g., crystalline or amorphous forms) of berberine ursodeoxycholate and pharmaceutical compositions thereof useful in treating and/or preventing various diseases or disorders, including metabolic disorders, heart diseases, neurodegenerative diseases and liver diseases.

BACKGROUND OF THE INVENTION

The compound berberine ursodeoxycholate "BBR-UDCA", represented by

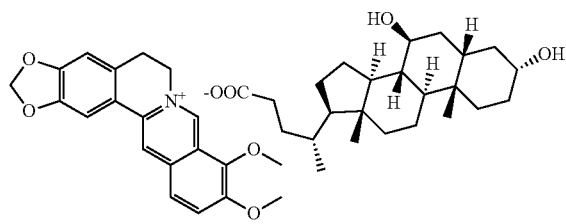

Berberine Ursodeoxycholate (BBR-UDCA)

was disclosed in WO 2016/015634A1 (PCT/CN2015/085350, filed Jul. 28, 2015, priority date Jul. 29, 2014), the content of which is incorporated herein by reference in its entirety. Preparation of the compound was disclosed therein as were certain beneficial biological activities of the compound.

Solid forms are of particular interest in the development of suitable dosage forms of pharmaceuticals. It is desirable to have processes for producing a compound with the selected solid form in high purity when the compound is used in clinical studies or commercial products since impurities present may produce undesired toxicological effects. If a solid form is not held constant during clinical or stability studies, the exact dosage form used or studied may not be comparable from one lot to another.

Certain solid forms may also exhibit enhanced thermodynamic stability or may be more readily manufactured in high purity in large quantities, and thus are more suitable for inclusion in pharmaceutical formulations. Different solid forms of an active pharmaceutical ingredient can lead to changes in the drug's solubility, dissolution rate, pharmacokinetics and ultimately its bioavailability and efficacy in patients. Certain solid forms may display other advantageous physical properties such as lack of hygroscopic tendencies, filterability, improved solubility, and enhanced rates of dissolution due to different lattice energies.

Thus, finding which solid form is the most stable under each condition of interest and the processes that lead to changes in a solid form is crucial to the design of the drug manufacturing process in order to ensure that the final product is in its preferred solid form. There remains an ongoing need to identify novel solid forms having desirable physicochemical properties suitable for preparation and therapeutic use.

SUMMARY OF THE INVENTION

The present invention provides novel solid forms (e.g., crystalline forms) of BBR-UDCA having one or more desirable properties, such as high stability, high crystallinity, high purity, low hygroscopicity, favorable dissolution and/or favorable mechanical properties. In particular, solid forms of BBR-UDCA disclosed herein provide improved physical stability and/or physicochemical properties suitable for clinical studies, product manufacture and therapeutic use.

The solid forms disclosed herein can be utilized to treat various diseases or disorders, such as diabetes, diabetic complications, dyslipidemia, dyslipidemia in statin-intolerance patients, hyperlipidemia, hypercholesterolemia, hypertriglyceridemia, diabetic dyslipidemia, obesity, metabolic syndromes, pre-diabetes, heart diseases, neurodegenerative diseases, sarcopenia, muscle atrophy, inflammation, and cancers as well as various liver diseases or disorders, such as fatty liver, non-alcoholic fatty liver disease, non-alcoholic steatohepatitis, cholestatic liver diseases or graft-versus-host disease of the liver. The compounds of this invention are also useful in improving liver functions in chronic viral associated liver diseases and alcohol-related liver diseases.

In one aspect, the invention generally relates to a solid form, which is Form A of BBR-UDCA, having an X-ray powder diffraction (XRPD) pattern comprising one or more peaks at 2θ values selected from the group consisting of: 3.98, 7.06, 7.34, 7.93, 8.79, 9.47, 11.70, 11.94, 12.34, 12.55, 13.90, 14.17, 15.14, 15.50, 16.16, 16.54, 16.78, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49° (±0.2°) obtained using Cu Kα radiation ($\lambda_1$=1.540598 Å, $\lambda_2$=1.544426 Å, intensity ratio $\lambda_2/\lambda_1$=0.50).

In another aspect, the invention generally relates to a solid form, which is Form B of BBR-UDCA, having an X-ray powder diffraction (XRPD) pattern comprising one or more peaks at 2θ values selected from the group consisting of: 7.39, 9.31, 12.41, 13.14, 14.37, 14.76, 15.53, 18.65, 21.79, 22.87, 25.27, 25.53 and 28.12° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form C of BBR-UDCA, having an X-ray powder diffraction (XRPD) pattern comprising one or more peaks at 2θ values selected from the group consisting of: 7.23, 10.42, 12.10, 13.37, 14.24, 14.48, 15.28, 15.95, 17.00, 18.17, 20.12, 21.77 and 25.47° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form D of BBR-UDCA, having an X-ray powder diffraction (XRPD) pattern comprising one or more peaks at 2θ values selected from the group consisting of: 4.24, 6.79, 8.50, 10.25, 11.50, 13.62, 14.74, 15.20, 17.92, 18.39, 22.91 and 25.73° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form E of BBR-UDCA, having an X-ray powder diffraction (XRPD) pattern comprising one or more peaks at 2θ values selected from the group consisting of: 8.59, 10.55, 11.36, 11.86, 12.46, 13.08, 13.38, 14.34, 15.57, 17.24, 17.72, 18.43, 19.66, 19.84, 20.35, 20.91, 21.36, 21.95, 23.21, 24.67, 25.04, 25.82, 26.12, 27.01, 27.84, 28.97, 30.35, 33.33, 34.54 and 36.06° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form H of BBR-UDCA, having an X-ray powder diffraction (XRPD) pattern comprising one or more peaks at 2θ values selected from the group consisting of: 13.05, 14.63 and 25.46° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form I of BBR-UDCA, having an X-ray powder diffraction (XRPD) pattern comprising one or more peaks at 2θ values selected from the group consisting of: 4.19, 7.64, 10.03, 13.32, 13.84, 14.83, 16.73, 22.73, 25.61 and 28.57° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form J of BBR-UDCA, having an X-ray powder diffraction (XRPD) pattern comprising one or more peaks at 2θ values selected from the group consisting of: 4.61, 6.32, 7.38, 8.22, 9.21, 10.57, 11.73, 12.13, 12.62, 12.96, 13.87, 14.55, 14.78, 15.81, 16.48, 17.69, 18.39, 19.01, 20.06, 21.25, 22.13, 23.20, 24.47, 24.89, 26.31, 27.98, 30.25 and 33.35° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form P of BBR-UDCA, having an X-ray powder diffraction (XRPD) pattern comprising one or more peaks at 2θ values selected from the group consisting of: 3.11, 5.01, 5.78, 7.26, 9.20, 10.10, 10.79, 11.65, 13.70, 14.59, 15.22, 16.19, 16.54, 17.05, 18.06, 18.68, 20.52, 21.09, 21.73, 22.49, 24.73, 25.42, 25.94 and 30.11° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form W of BBR-UDCA, having an X-ray powder diffraction (XRPD) pattern comprising one or more peaks at 2θ values selected from the group consisting of: 6.49, 7.16, 8.51, 10.21, 12.01, 13.13, 13.90, 14.42, 15.18, 15.57, 16.03, 16.45, 16.74, 17.08, 17.85, 18.39, 19.61, 20.43, 21.39, 21.70, 23.51 and 25.21° (±0.2°) obtained using Cu Kα radiation ($\lambda_1$=1.540598 Å, $\lambda_2$=1.544426 Å, intensity ratio $\lambda_2/\lambda_1$=0.50).

In yet another aspect, the invention generally relates to a solid form, which is Form X of BBR-UDCA, having an X-ray powder diffraction (XRPD) pattern comprising one or more peaks at 2θ values selected from the group consisting of: 3.63, 6.61, 7.24, 10.49, 11.95, 13.51, 14.26, 14.54, 15.14, 16.01, 16.82, 18.28, 20.26, 21.08, 21.49, 21.90, 25.60, 26.40, 27.31, 29.34, 30.59, 31.01, 34.04, 34.68 and 36.91° (±0.2°) obtained using Cu Kα radiation ($\lambda_1$=1.540598 Å, =1.544426 Å, intensity ratio $\lambda_1/\lambda_1$=0.50).

In yet another aspect, the invention generally relates to a solid form of hemi-nonahydrate of BBR-UDCA.

In yet another aspect, the invention generally relates to a composition comprising one or more solid forms disclosed herein (e.g., one or more of Forms A, B, C, D, E, H, I, J, P, W, and X).

In yet another aspect, the invention generally relates to a composition comprising two or more solid forms disclosed herein (e.g., two or more of Forms A, B, C, D, E, H, I, J, P, W, and X).

In yet another aspect, the invention generally relates to a pharmaceutical composition comprising Form A of BBR-UDCA and a pharmaceutically acceptable excipient, carrier, or diluent.

In yet another aspect, the invention generally relates to a pharmaceutical composition comprising Form B of BBR-UDCA and a pharmaceutically acceptable excipient, carrier, or diluent.

In yet another aspect, the invention generally relates to a pharmaceutical composition comprising Form C of BBR-UDCA and a pharmaceutically acceptable excipient, carrier, or diluent.

In yet another aspect, the invention generally relates to a pharmaceutical composition comprising Form D of BBR-UDCA and a pharmaceutically acceptable excipient, carrier, or diluent.

In yet another aspect, the invention generally relates to a pharmaceutical composition comprising Form E of BBR-UDCA and a pharmaceutically acceptable excipient, carrier, or diluent.

In yet another aspect, the invention generally relates to a pharmaceutical composition comprising Form H of BBR-UDCA and a pharmaceutically acceptable excipient, carrier, or diluent.

In yet another aspect, the invention generally relates to a pharmaceutical composition comprising Form I of BBR-UDCA and a pharmaceutically acceptable excipient, carrier, or diluent.

In yet another aspect, the invention generally relates to a pharmaceutical composition comprising Form J of BBR-UDCA and a pharmaceutically acceptable excipient, carrier, or diluent.

In yet another aspect, the invention generally relates to a pharmaceutical composition comprising Form P of BBR-UDCA and a pharmaceutically acceptable excipient, carrier, or diluent.

In yet another aspect, the invention generally relates to a pharmaceutical composition comprising Form W of BBR-UDCA and a pharmaceutically acceptable excipient, carrier, or diluent.

In yet another aspect, the invention generally relates to a pharmaceutical composition comprising Form X of BBR-UDCA and a pharmaceutically acceptable excipient, carrier, or diluent.

In yet another aspect, the invention generally relates to a unit dosage form comprising a pharmaceutical composition disclosed herein.

In yet another aspect, the invention generally relates to a method for treating, reducing, or preventing a metabolic disorder, a heart disease, a neurodegenerative disease, or a liver disease, comprising administering to a subject in need thereof a therapeutically effective amount of a pharmaceutical composition disclosed herein.

In yet another aspect, the invention generally relates to a method for treating, reducing, or preventing a disease or disorder, comprising administering to a subject in need thereof a therapeutically effective amount of a pharmaceutical composition disclosed herein or a unit dosage form disclosed herein, effective to treat, prevent, or reduce one or more diseases or disorders selected from fatty liver, non-alcoholic fatty liver disease (NAFLD) and non-alcoholic steatohepatitis (NASH), cholestatic liver diseases, graft-versus-host disease of the liver, primary sclerosing cholangitis, chronic viral associated liver diseases, alcohol-related liver diseases, metabolic diseases or disorders such as pre-diabetes, diabetes, hyperlipidemia, hypercholesterolemia, diabetic dyslipidemia, dyslipidemia in statin-intolerant patients, obesity, or a related disease or disorder thereof in a mammal, including a human.

In yet another aspect, the invention generally relates to a method for preparing Form A of berberine ursodeoxycholate. The method includes: forming a mixture of a crystalline and/or amorphous form of berberine ursodeoxycholate with co-solvents of an organic solvent and $H_2O$, wherein the water activity is greater than about 0.4; stirring the mixture at room temperature; filtering the mixture to obtain a filter cake; washing the filter cake with distilled water; and removing water to obtain Form A of berberine ursodeoxycholate.

In yet another aspect, the invention generally relates to a method for preparing Form B of berberine ursodeoxycholate. The method includes: forming a mixture of a crystalline and/or amorphous form of berberine ursodeoxycholate with acetonitrile/$H_2O$, wherein the acetonitrile:$H_2O$ (v/v) is from about 1:2 to about 2:1; and slowly evaporating to remove acetonitrile/$H_2O$ to obtain Form B of berberine ursodeoxycholate.

In yet another aspect, the invention generally relates to a method for preparing Form C of berberine ursodeoxycholate. The method includes: forming a mixture of a crystalline and/or amorphous form of berberine ursodeoxycholate with isopropyl alcohol/isopropyl acetate, wherein the isopropyl alcohol:isopropyl acetate (v/v) is from about 1:2 to about 2:1; and slowly evaporating to remove isopropyl alcohol/isopropyl acetate to obtain Form C of berberine ursodeoxycholate.

In yet another aspect, the invention generally relates to a method for preparing Form D of berberine ursodeoxycholate. The method includes: forming a mixture of crystalline and/or amorphous form of berberine ursodeoxycholate with an organic solvent or an organic solvent/water co-solvents having a water activity less than about 0.2; stirring the mixture at room temperature; and filtering the mixture to obtain Form D of berberine ursodeoxycholate.

In yet another aspect, the invention generally relates to a method for preparing Form E of berberine ursodeoxycholate. The method includes: providing Form A of berberine ursodeoxycholate; and performing solid vapor diffusion in a dichloromethane atmosphere to obtain Form E of berberine ursodeoxycholate.

In yet another aspect, the invention generally relates to a method for preparing Form H of berberine ursodeoxycholate. The method includes: dissolving a crystalline and/or amorphous form of berberine ursodeoxycholate in acetonitrile/$H_2O$, wherein the acetonitrile:$H_2O$ (v/v) is from about 1:2 to about 2:1; slowly evaporating acetonitrile/$H_2O$; collecting precipitate by filtration; heating the obtained precipitate to about 100° C.; and cooling heated precipitate to room temperature to obtain Form H of berberine ursodeoxycholate.

In yet another aspect, the invention generally relates to a method for preparing Form I of berberine ursodeoxycholate. The method includes: dissolving a crystalline and/or amorphous form of berberine ursodeoxycholate in tetrahydrofuran/$H_2O$, wherein the tetrahydrofuran:$H_2O$ (v/v) is from about 1:2 to about 2:1; slowly evaporating tetrahydrofuran/$H_2O$; and collecting the precipitate by filtration to obtain Form I of berberine ursodeoxycholate.

In yet another aspect, the invention generally relates to a method for preparing Form J of berberine ursodeoxycholate. The method includes: providing Form A of berberine ursodeoxycholate; heating Form A of berberine ursodeoxycholate to about 100° C. in $N_2$; and cooling the heated berberine ursodeoxycholate under $N_2$ to room temperature to obtain Form J of berberine ursodeoxycholate.

In yet another aspect, the invention generally relates to a method for preparing Form P of berberine ursodeoxycholate. The method includes: providing Form A of berberine ursodeoxycholate; slurrying Form A of berberine ursodeoxycholate in MeOH/methyl ethyl ketone or MeOH/methy tert-butyl ether, wherein the MeOH:methyl ethyl ketone (v/v) is from about 1:8 to about 1:10 or MeOH:methyl tert-butyl ether (v/v) is from about 1:8 to about 1:10 at about 50° C.; and collecting the solid to obtain Form P of berberine ursodeoxycholate.

In yet another aspect, the invention generally relates to a method for preparing Form W of berberine ursodeoxycholate. The method includes: providing Form A of berberine ursodeoxycholate; slurrying Form A of berberine ursodeoxycholate in cyclohexanone/n-butylacetate, wherein the cyclohexanone:n-butylacetate (v/v) is from about 1:3 to about 1:5 at room temperature; and collecting the solid to obtain Form W of berberine ursodeoxycholate.

In yet another aspect, the invention generally relates to a method for preparing Form X of berberine ursodeoxycholate. The method includes: providing Form A of berberine ursodeoxycholate; dissolving Form A of berberine ursodeoxycholate in n-butanol; slowly evaporating n-butanol at room temperature; and collecting the precipitate by filtration to obtain Form X of berberine ursodeoxycholate.

DEFINITIONS

Figure 1:
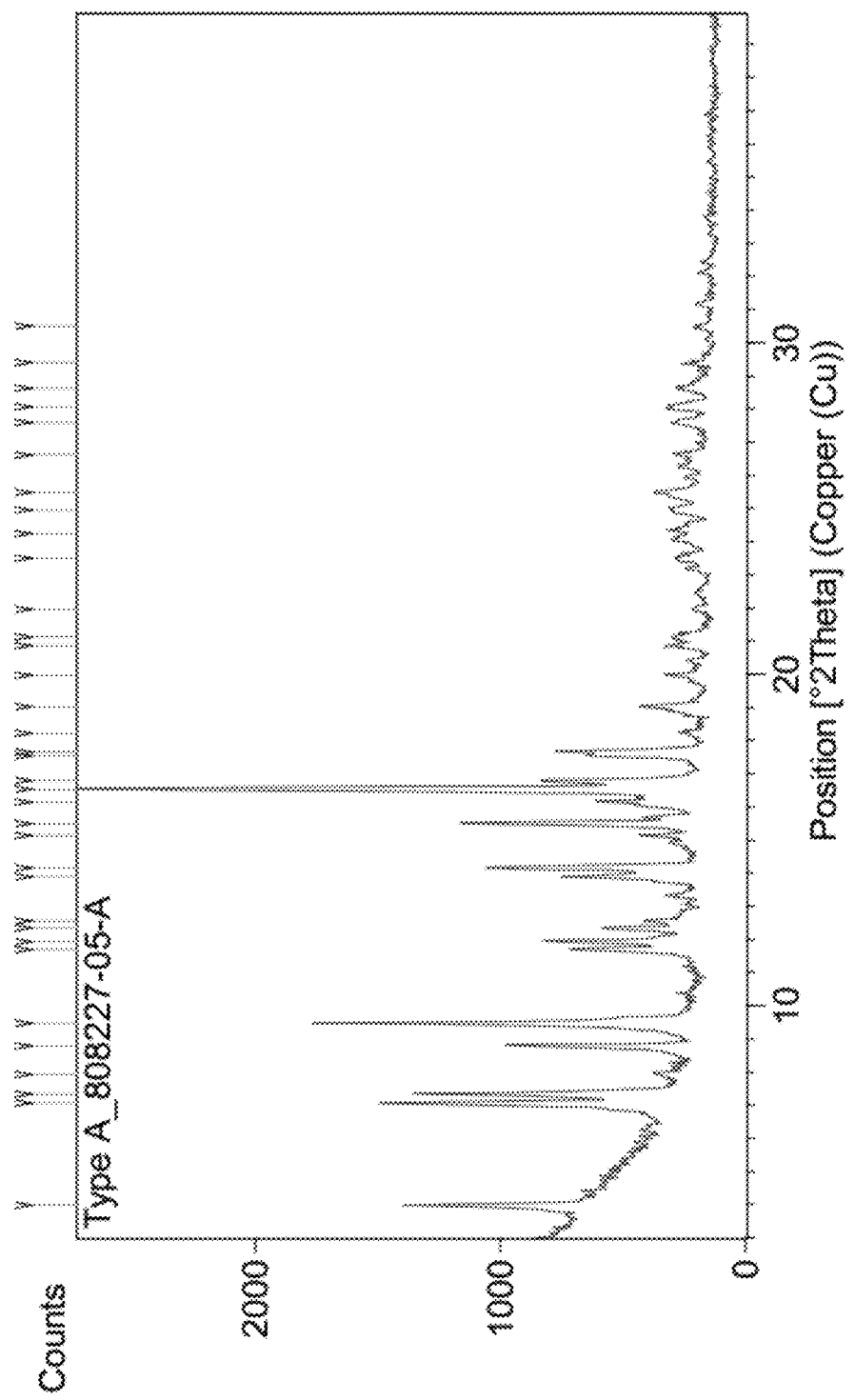
FIG. 1 shows an embodiment of XRPD pattern of Form A of BBR-UDCA.

The terms used herein have their ordinary meaning and the meaning of such terms is independent at each occurrence thereof. That notwithstanding and except where stated otherwise, the following definitions apply throughout the specification and claims.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degrees, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

Similarly, as used herein, "essentially the same" with reference to differential scanning calorimetry (DSC) is intended to also encompass the variability associated with these analytical techniques, which are known to those of skill in the art.

As used herein, the term "stable" refers to a compound that is not substantially altered when subjected to conditions to allow for its production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week, preferably for at least a month, more preferably for at least six months, even more preferably for at least one year.

As used herein, the term "solvate" refers to a crystalline solid adduct containing either stoichiometric or nonstoichiometric amounts of a solvent incorporated within the crystal structure. When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be nonstoichiometric. If the incorporated solvent is water, such adduct is referred to as a "hydrate". Thus, the term "hydrate" describes a solvate comprising the drug substance and a stoichiometric or nonstoichiometric amount of water.

A compound of the present invention is, subsequent to its preparation, preferably isolated and purified to obtain a composition containing an amount by weight equal to or greater than 95%, which is then used or formulated as described herein. In certain embodiments, a compound of the invention is more than 99% pure. As used herein, the term "substantially pure" with reference to a particular crystalline or amorphous form means that the crystalline or amorphous form includes less than 10%, preferably less than 5%, more preferably less than 3%, even more preferably less than 1% by weight of any other physical forms of the compound.

As used herein, the term "crystalline" refers to any solid substance exhibiting three-dimensional order, which in contrast to an amorphous solid substance, gives a distinctive X-ray powder diffraction (XRPD) pattern with sharply defined peaks.

As used herein, the term "amorphous" refers to any solid substance that lacks order in three dimensions. In some instances, amorphous solids may be characterized by known techniques, including X-ray powder diffraction (XRPD) crystallography, solid-state nuclear magnet resonance (ssNMR) spectroscopy, differential scanning calorimetry (DSC), or some combination of these techniques. Amorphous solids give diffuse XRPD patterns, typically comprised of one or two broad peaks (i.e., peaks having base widths of about 5° 2 θ. or greater).

As used herein, the term "polymorph" refers to different crystalline forms of the same compound and includes, but is not limited to, other solid state molecular forms including hydrates (e.g., bound water present in the crystalline structure) and solvates (e.g., bound solvents other than water) of the same compound.

As used herein, the term "X-ray powder diffraction pattern" or "XRPD pattern" refers to the experimentally observed diffractogram or parameters derived therefrom.

X-Ray powder diffraction patterns are characterized by peak position (abscissa) and peak intensities (ordinate).

As used herein, the term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein. For example, as described herein, CuKα (wavelength: $\lambda_1$=1.540598 Å, $\lambda_2$=1.544426 Å, intensity ratio $\lambda_2/\lambda_1$=0.50) was used as the source of radiation.

As used herein, the term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

As used herein, the term "treating, reducing, or preventing a disease or disorder" refers to ameliorating such a condition before or after it has occurred. As compared with an equivalent untreated control, such reduction or degree of prevention is at least 5%, 10%, 20%, 40%, 50%, 60%, 80%, 90%, 95%, or 100% as measured by any standard technique.

As used herein, the term "pharmaceutically acceptable excipient, carrier, or diluent" refers to a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

As used herein, the "an amount sufficient" refers to the amount of a compound, alone or in combination with another therapeutic regimen, required to treat, prevent, or reduce a metabolic disorder such as diabetes in a clinically relevant manner. A sufficient amount of an active compound used to practice the present invention for therapeutic treatment of conditions varies depending upon the manner of administration, the age, body weight, and general health of the mammal or patient. Ultimately, the prescribers will decide the appropriate amount and dosage regimen. Additionally, an effective amount may be an amount of compound that is safe and efficacious in the treatment of a patient as determined and approved by a regulatory authority (such as the U.S. Food and Drug Administration).

As used herein, the "low dosage" refers to at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of an agent that reduces glucose levels and that is formulated for administration by inhalation will differ from a low dosage of the same agent formulated for oral administration.

As used herein, the "high dosage" is meant at least 5% (e.g., at least 10%, 20%, 50%, 100%, 200%, or even 300%) more than the highest standard recommended dosage of a particular compound for treatment of any human disease or condition.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

DETAILED DESCRIPTION OF THE INVENTION

The present invention is based in part on the unexpected discovery of novel solid forms (e.g., crystalline forms) of berberine ursodeoxycholate (BBR-UDCA) having one or more desirable properties, such as high stability, high crystallinity, high purity, low hygroscopicity, favorable dissolution and/or favorable mechanical properties. In particular, solid forms of BBR-UDCA disclosed herein provide improved physical stability and/or physicochemical properties suitable for clinical studies, product manufacture and therapeutic use.

While multiple solid forms of BBR-UDCA have been identified, each solid form can be uniquely identified by different analytical parameters, alone or in combination, such as, but not limited to: X-ray powder diffraction pattern (XRPD) peaks or combinations of two or more peaks; thermo gravimetric analysis (TGA); differential scanning calorimetry (DSC); dynamic vapor sorption (DVS); polarized light microscope (PLM); high-performance liquid chromatography (HPLC); and nuclear magnetic resonance (NMR).

Diseases and disorders that may be treated and/or prevented by the compounds, pharmaceutical compositions and methods disclosed herein include such as diabetes, diabetic complications, dyslipidemia, dyslipidemia in statin-intolerance patients, hyperlipidemia, hypercholesterolemia, hypertriglyceridemia, diabetic dyslipidemia, obesity, metabolic syndromes, pre-diabetes, atherosclerosis, heart diseases, neurodegenerative diseases, sarcopenia, muscle atrophy, inflammation, cancer and liver diseases and conditions such as fatty liver, non-alcoholic fatty liver disease, non-alcoholic steatohepatitis, cholestatic liver diseases or graft-versus-host disease of the liver. The compounds of this invention are also useful in improving liver functions in chronic viral associated liver diseases and alcohol-related liver diseases.

In one aspect, the invention generally relates to a solid form, which is Form A of BBR-UDCA, having an X-ray powder diffraction (XRPD) pattern comprising one or more peaks at 2θ values selected from the group consisting of: 3.98, 7.06, 7.34, 7.93, 8.79, 9.47, 11.70, 11.94, 12.34, 12.55, 13.90, 14.17, 15.14, 15.50, 16.16, 16.54, 16.78, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form A of BBR-UDCA) has an X-ray powder diffraction (XRPD) pattern comprising peaks at 2θ values of 3.98, 7.06, 7.34, 8.79 and 16.54° (±0.2°).

In certain embodiments, the solid form (Form A of BBR-UDCA) has an X-ray powder diffraction (XRPD) pattern comprising peaks at 2θ values of 3.98, 7.06, 7.34, 8.79, 9.47, 11.94, 13.90, 14.17, 15.50, 16.16, 16.54, 16.78 and 17.67° (±0.2°).

In certain embodiments, the solid form (Form A of BBR-UDCA) has an X-ray powder diffraction (XRPD) pattern comprising peaks at 2θ values of 3.98, 7.06, 7.34, 7.93, 8.79, 9.47, 11.70, 11.94, 12.34, 12.55, 13.90, 14.17, 15.14, 15.50, 16.16, 16.54, 16.78, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49° (±0.2°).

In certain embodiments, the solid form (Form A of BBR-UDCA) is a hydrate of BBR-UDCA. In certain embodiments, the solid form (Form A of BBR-UDCA) is a hemi-nonahydrate of BBR-UDCA.

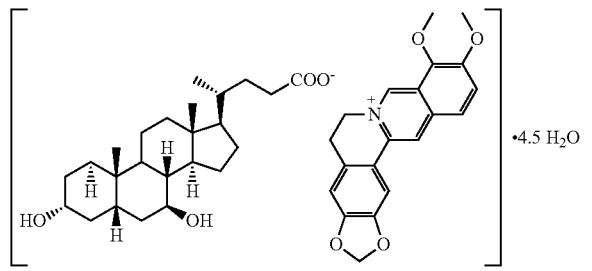

Hemi-nonahydrate of berberine ursodeoxycholate (BBR-UDCA)

Figure 19:
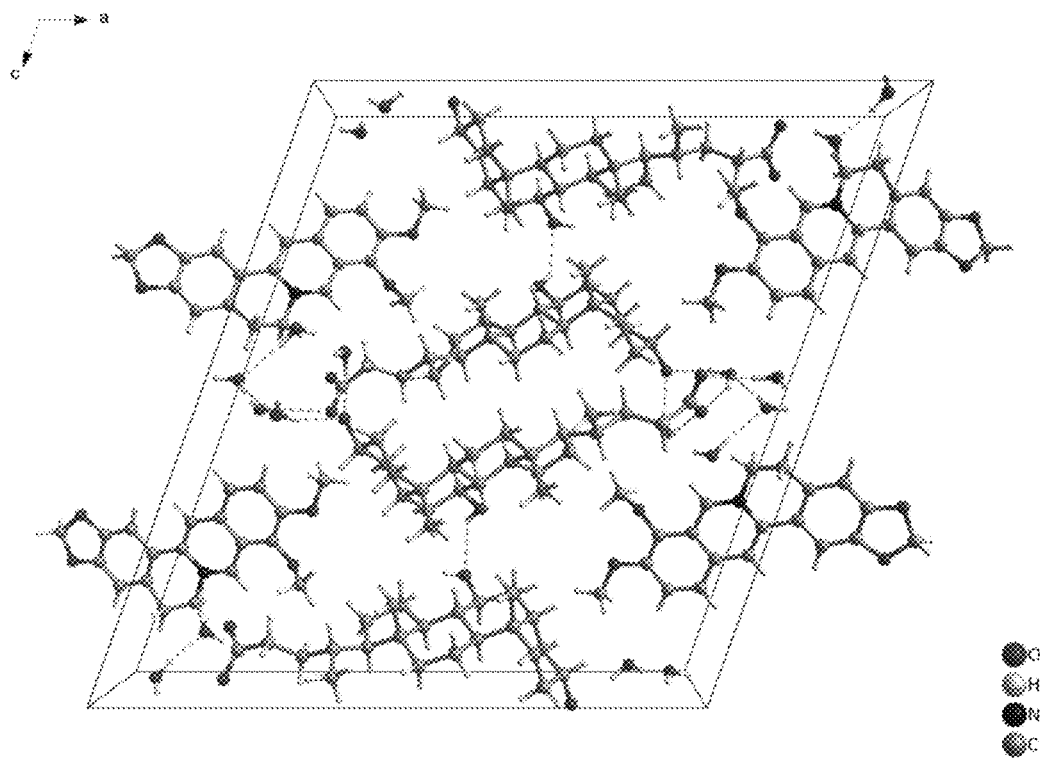
FIG. 19 depicts a unit cell of single crystalline Form A of BBR-UDCA.

In certain embodiments, the solid form (Form A of BBR-UDCA) is crystalline. In certain embodiments, the crystalline form is characterized in a monoclinic crystal system and $P2_1$ space group. In certain embodiments of the crystalline form, each unit cell contains two asymmetric units and there are two BBR cations, two UDCA anions and nine $H_2O$ molecules per asymmetric unit, and four BBR cations, four UDCA anions and eighteen $H_2O$ molecules per unit cell. (FIG. 19.)

In certain embodiments, the solid form (Form A of BBR-UDCA) is characterized by an X-ray powder diffraction (XRPD) pattern comprising peaks at diffraction angles 2θ essentially the same as the one presented in FIG. 1.

In certain embodiments, the solid form (Form A of BBR-UDCA) is characterized by a purity of 70% or higher.

In certain embodiments, the solid form (Form A of BBR-UDCA) is characterized by a purity of 95% or higher.

In another aspect, the invention generally relates to a solid form, which is Form B of BBR-UDCA, having an X-ray powder diffraction (XRPD) pattern comprising one or more peaks at 2θ values selected from the group consisting of: 7.39, 9.31, 12.41, 13.14, 14.37, 14.76, 15.53, 18.65, 21.79, 22.87, 25.27, 25.53 and 28.12)° (±0.2° obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form B of BBR-UDCA) has an X-ray powder diffraction (XRPD) pattern comprising peaks at 2θ values of 9.31, 12.41, 15.53, 18.65, 21.79, 22.87, and 25.53° (±0.2°).

In certain embodiments, the solid form (Form B of BBR-UDCA) has an X-ray powder diffraction (XRPD) pattern comprising peaks at 2θ values of 7.39, 9.31, 12.41, 13.14, 14.37, 14.76, 15.53, 18.65, 21.79, 22.87, 25.27, 25.53 and 28.12° (±0.2°).

In certain embodiments, the solid form (Form B of BBR-UDCA) is a hydrate of berberine ursodeoxycholate.

Figure 2:
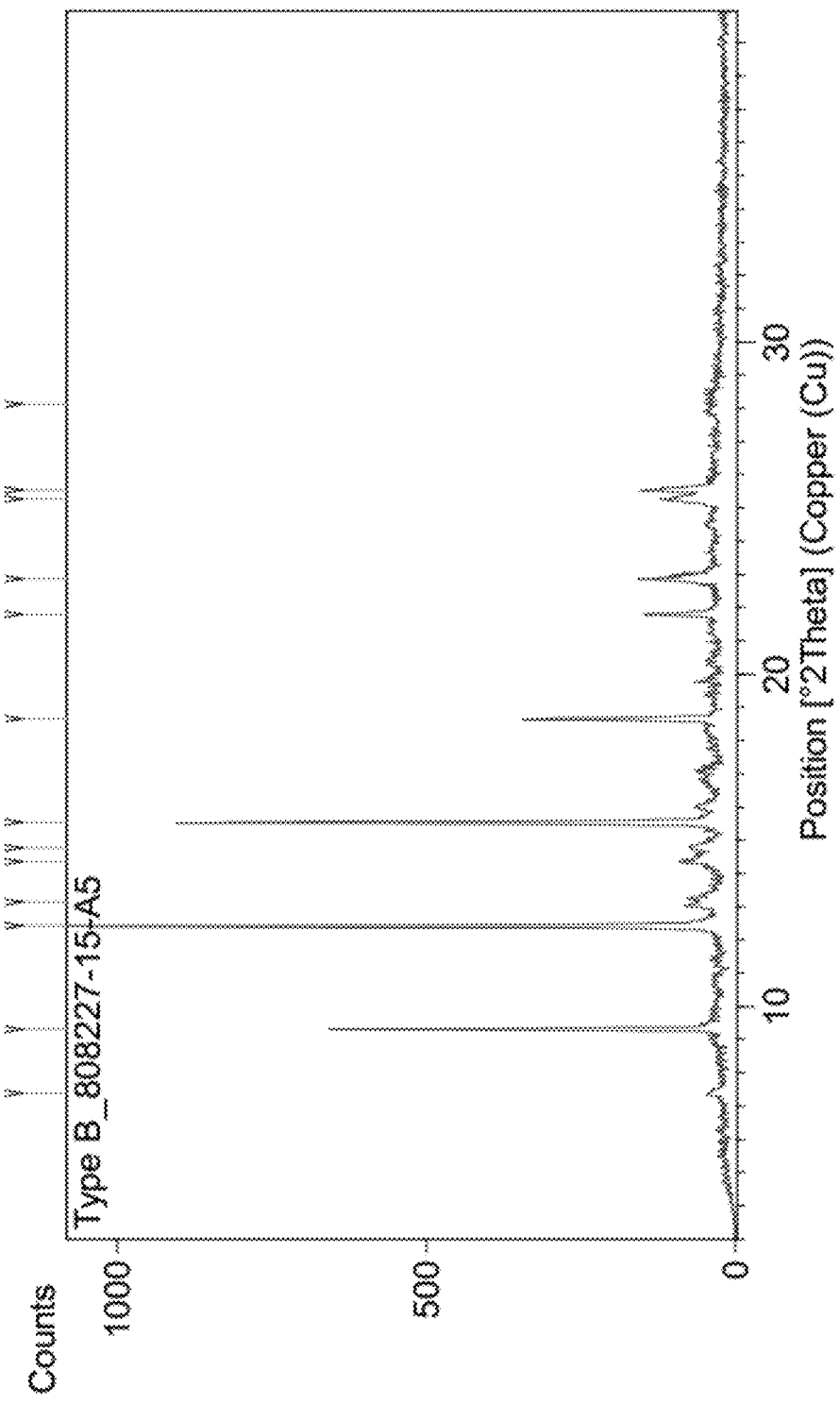
FIG. 2 shows an embodiment of XRPD pattern of Form B of BBR-UDCA.

In certain embodiments, the solid form (Form B of BBR-UDCA) is characterized by an X-ray powder diffraction (XRPD) pattern comprising peaks at diffraction angles 2θ essentially the same as the one presented in FIG. 2.

In certain embodiments, the solid form (Form B of BBR-UDCA) is characterized by a differential scanning calorimetry (DSC) curve comprising an endotherm at about 78.1° C. (onset temperature) and an endotherm at about 91.2° C. (onset temperature).

Figure 20:
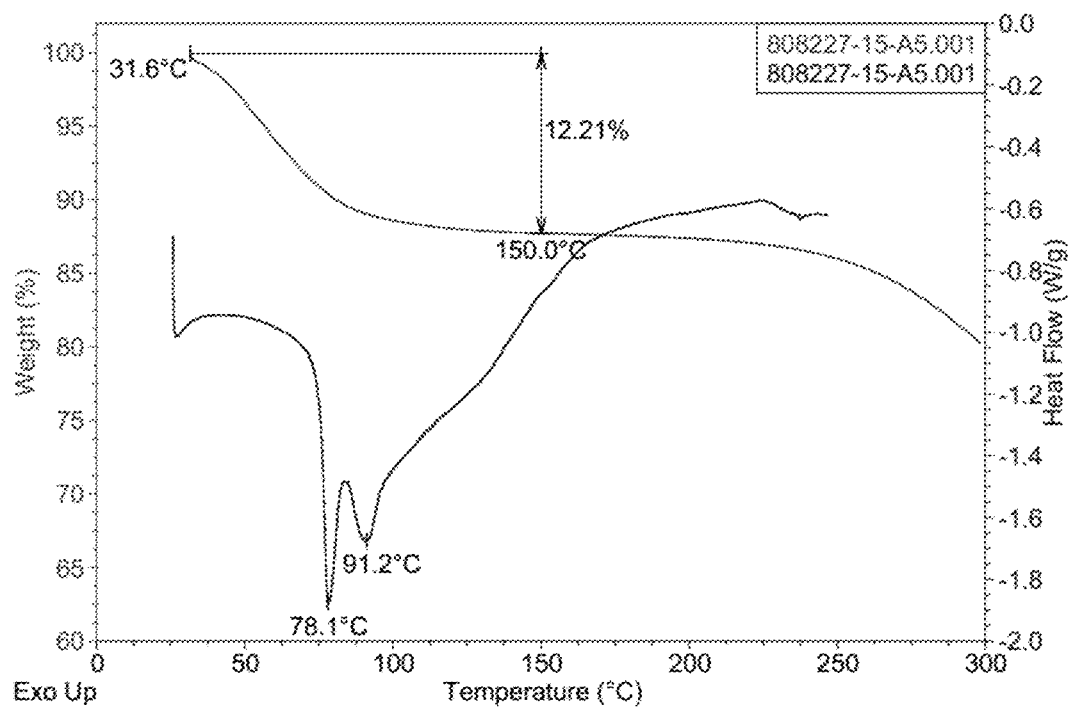
FIG. 20 shows an embodiment of a TGA/DSC graph of Form B of BBR-UDCA.

In certain embodiments, the solid form (Form B of BBR-UDCA) is characterized by a differential scanning calorimetry (DSC) curve essentially the same as the one presented in FIG. 20.

In certain embodiments, the solid form (Form B of BBR-UDCA) is characterized by a purity of 70% or higher.

In certain embodiments, the solid form (Form B of BBR-UDCA) is characterized by a purity of 95% or higher.

In yet another aspect, the invention generally relates to a solid form, which is Form C of BBR-UDCA, having an X-ray powder diffraction (XRPD) pattern comprising one or more peaks at 2θ values selected from the group consisting of: 7.23, 10.42, 12.10, 13.37, 14.24, 14.48, 15.28, 15.95, 17.00, 18.17, 20.12, 21.77 and 25.47° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form C of BBR-UDCA) has an X-ray powder diffraction (XRPD) pattern comprising peaks at 2θ values of 7.23, 12.10, 13.37, 15.28, 18.17 and 21.77° (±0.2°).

In certain embodiments, the solid form (Form C of BBR-UDCA) has an X-ray powder diffraction (XRPD) pattern comprising peaks at 2θ values of 7.23, 10.42, 12.10, 13.37, 14.24, 14.48, 15.28, 15.95, 17.00, 18.17, 20.12, 21.77 and 25.47° (±0.2°).

In certain embodiments, the solid form (Form C of BBR-UDCA) is a hydrate of berberine ursodeoxycholate.

Figure 3:
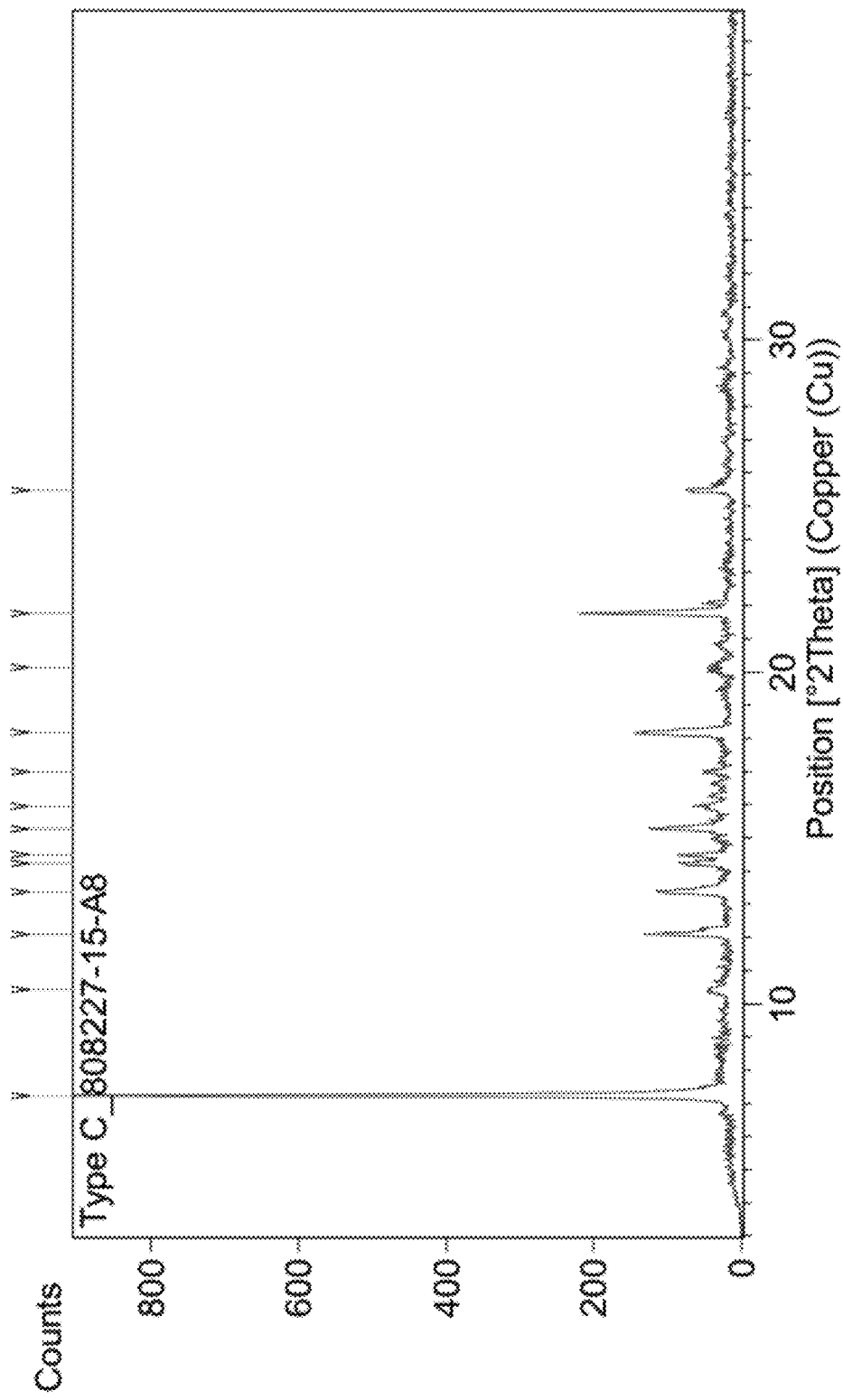
FIG. 3 shows an embodiment of XRPD pattern of Form C of BBR-UDCA.

In certain embodiments, the solid form (Form C of BBR-UDCA) is characterized by an X-ray powder diffraction (XRPD) pattern comprising peaks at diffraction angles 2θ essentially the same as the one presented in FIG. 3.

In certain embodiments, the solid form (Form C of BBR-UDCA) is characterized by a differential scanning calorimetry (DSC) curve comprising an endotherm at about 68.4° C. (onset temperature) and an endotherm at about 183.3° C. (onset temperature).

Figure 21:
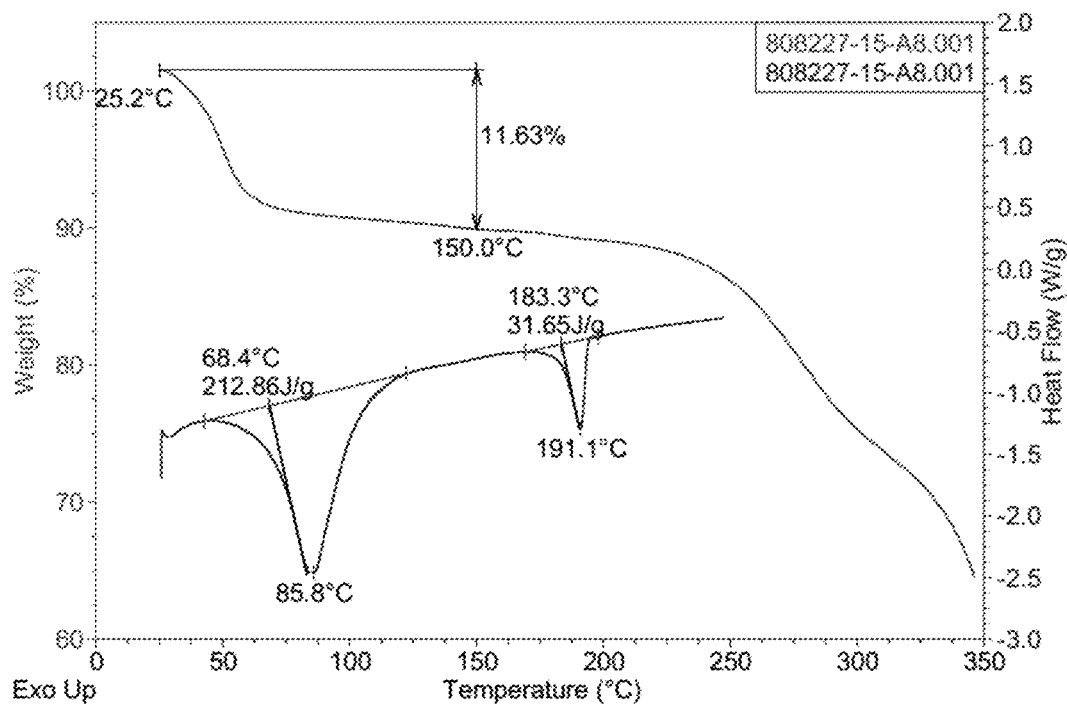
FIG. 21 shows an embodiment of a TGA/DSC graph of Form C of BBR-UDCA.

In certain embodiments, the solid form (Form C of BBR-UDCA) is characterized by a differential scanning calorimetry (DSC) curve essentially the same as the one presented in FIG. 21.

In certain embodiments, the solid form (Form C of BBR-UDCA) is characterized by a purity of 70% or higher.

In certain embodiments, the solid form (Form C of BBR-UDCA) is characterized by a purity of 95% or higher.

In yet another aspect, the invention generally relates to a solid form, which is Form D of BBR-UDCA, having an X-ray powder diffraction (XRPD) pattern comprising one or more peaks at 2θ values selected from the group consisting of: 4.24, 6.79, 8.50, 10.25, 11.50, 13.62, 14.74, 15.20, 17.92, 18.39, 22.91 and 25.73° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form D of BBR-UDCA) has an X-ray powder diffraction (XRPD) pattern comprising peaks at 2θ values of 4.24, 6.79, 8.50, 13.62 and 15.20° (±0.2°).

In certain embodiments, the solid form (Form D of BBR-UDCA) has an X-ray powder diffraction (XRPD) pattern comprising peaks at 2θ values of 4.24, 6.79, 8.50, 10.25, 11.50, 13.62, 14.74, 15.20, 17.92 and 25.73°±(0.2°).

In certain embodiments, the solid form (Form D of BBR-UDCA) has an X-ray powder diffraction (XRPD) pattern comprising peaks at 2θ values of 4.24, 6.79, 8.50, 10.25, 11.50, 13.62, 14.74, 15.20, 17.92, 18.39, 22.91 and 25.73° (±0.2°).

In certain embodiments, the solid form (Form D of BBR-UDCA) is an anhydrous berberine ursodeoxycholate.

In certain embodiments, the solid form (Form D of BBR-UDCA) is crystalline.

Figure 4:
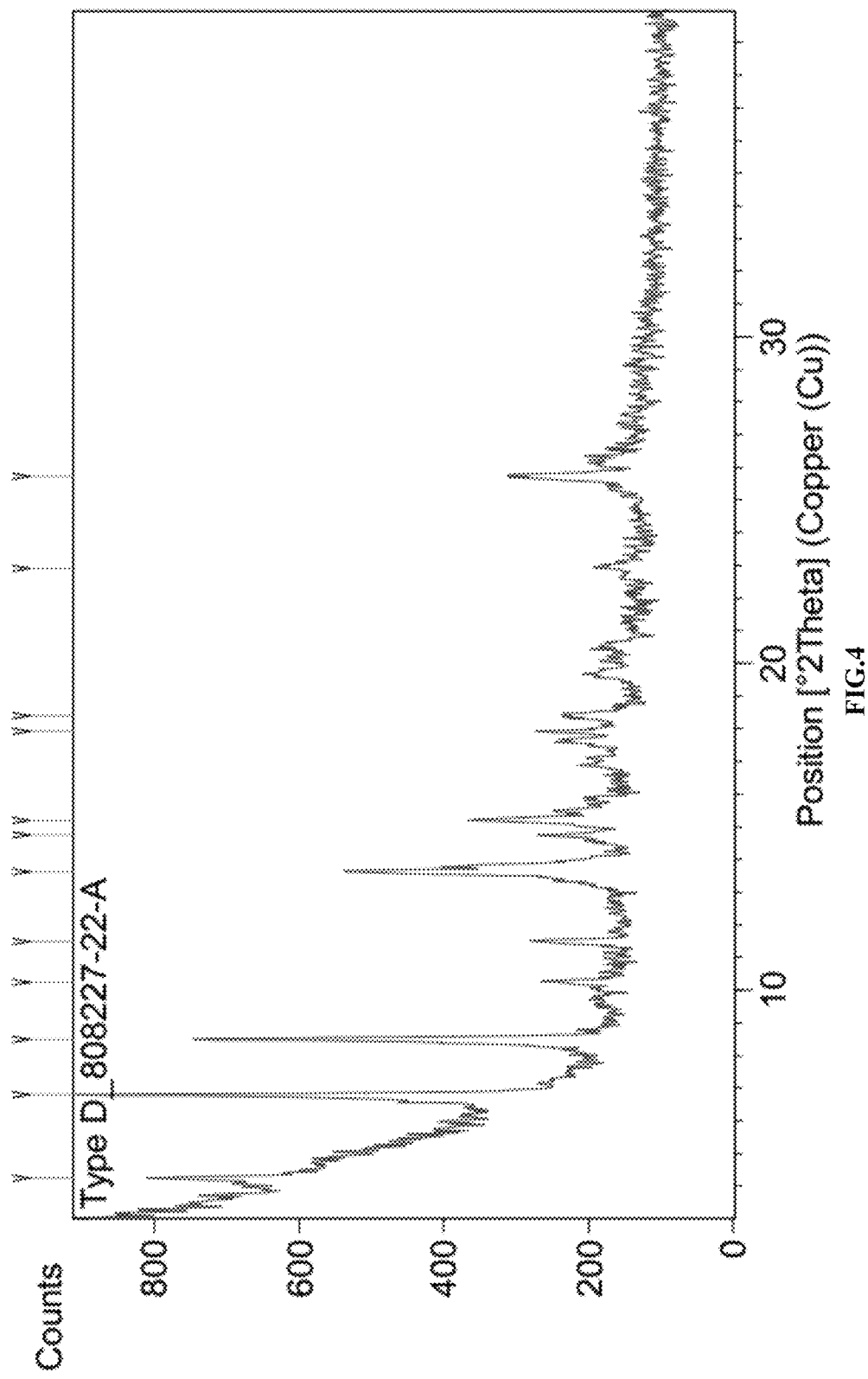
FIG. 4 shows an embodiment of XRPD pattern of Form D of BBR-UDCA.

In certain embodiments, the solid form (Form D of BBR-UDCA) is characterized by an X-ray powder diffraction (XRPD) pattern comprising peaks at diffraction angles 2θ essentially the same as the one presented in FIG. 4.

In certain embodiments, the solid form (Form D of BBR-UDCA) is characterized by a differential scanning calorimetry (DSC) curve comprising an endotherm at about 185.2° C. (onset temperature).

Figure 22:
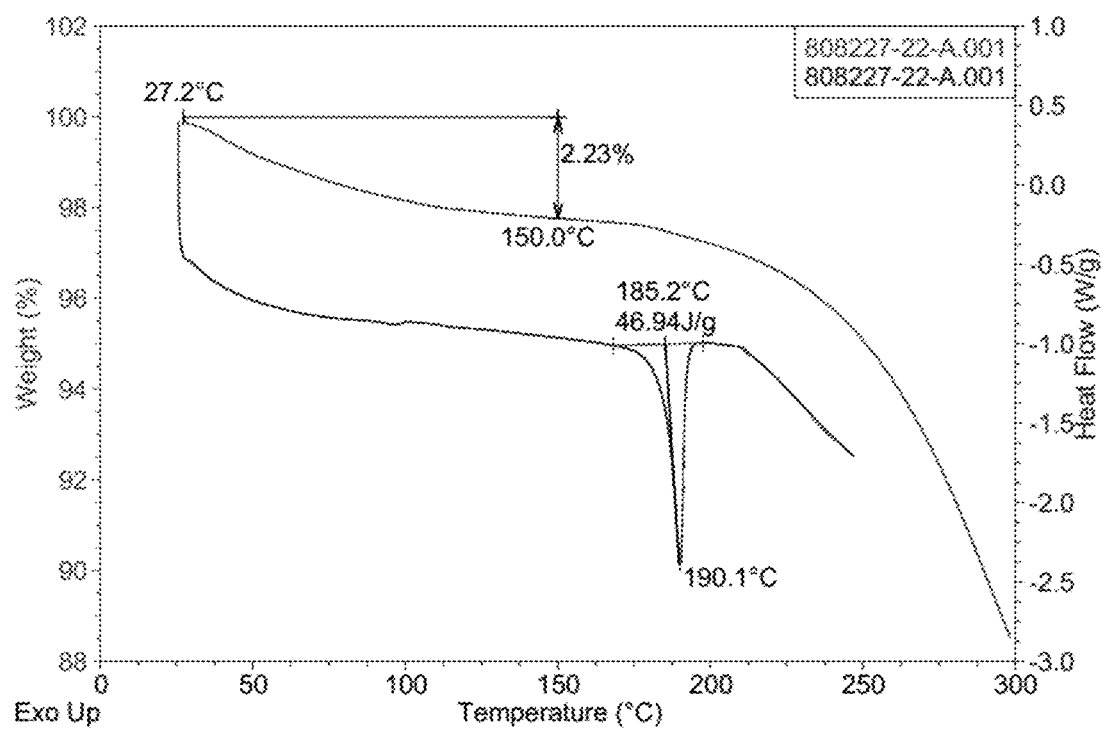
FIG. 22 shows an embodiment of a TGA/DSC graph of Form D of BBR-UDCA.

In certain embodiments, the solid form (Form D of BBR-UDCA) is characterized by a differential scanning calorimetry (DSC) curve essentially the same as the one presented in FIG. 22.

In certain embodiments, the solid form (Form D of BBR-UDCA) is characterized by a purity of 70% or higher.

In certain embodiments, the solid form (Form D of BBR-UDCA) is characterized by a purity of 95% or higher.

In yet another aspect, the invention generally relates to a solid form, which is Form E of BBR-UDCA, having an X-ray powder diffraction (XRPD) pattern comprising one or more peaks at 2θ values selected from the group consisting of: 8.59, 10.55, 11.36, 11.86, 12.46, 13.08, 13.38, 14.34, 15.57, 17.24, 17.72, 18.43, 19.66, 19.84, 20.35, 20.91, 21.36, 21.95, 23.21, 24.67, 25.04, 25.82, 26.12, 27.01, 27.84, 28.97, 30.35, 33.33, 34.54 and 36.06° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form E of BBR-UDCA) has an X-ray powder diffraction (XRPD) pattern comprising peaks at 2θ values of 11.36, 17.24, 17.72 and 20.91° (±0.2°).

In certain embodiments, the solid form (Form E of BBR-UDCA) has an X-ray powder diffraction (XRPD) pattern comprising peaks at 2θ values of 10.55, 11.36, 12.46, 13.08, 13.38, 14.34, 17.24, 17.72, 19.66, 19.84, 20.35, 20.91, 21.36 and 21.95° (±0.2°).

In certain embodiments, the solid form (Form E of BBR-UDCA) has an X-ray powder diffraction (XRPD) pattern comprising peaks at 2θ values of: 8.59, 10.55, 11.36, 11.86, 12.46, 13.08, 13.38, 14.34, 15.57, 17.24, 17.72, 18.43, 19.66, 19.84, 20.35, 20.91, 21.36, 21.95, 23.21, 24.67, 25.04, 25.82, 26.12, 27.01, 27.84, 28.97, 30.35, 33.33, 34.54 and 36.06° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form E of BBR-UDCA) is crystalline.

Figure 5:
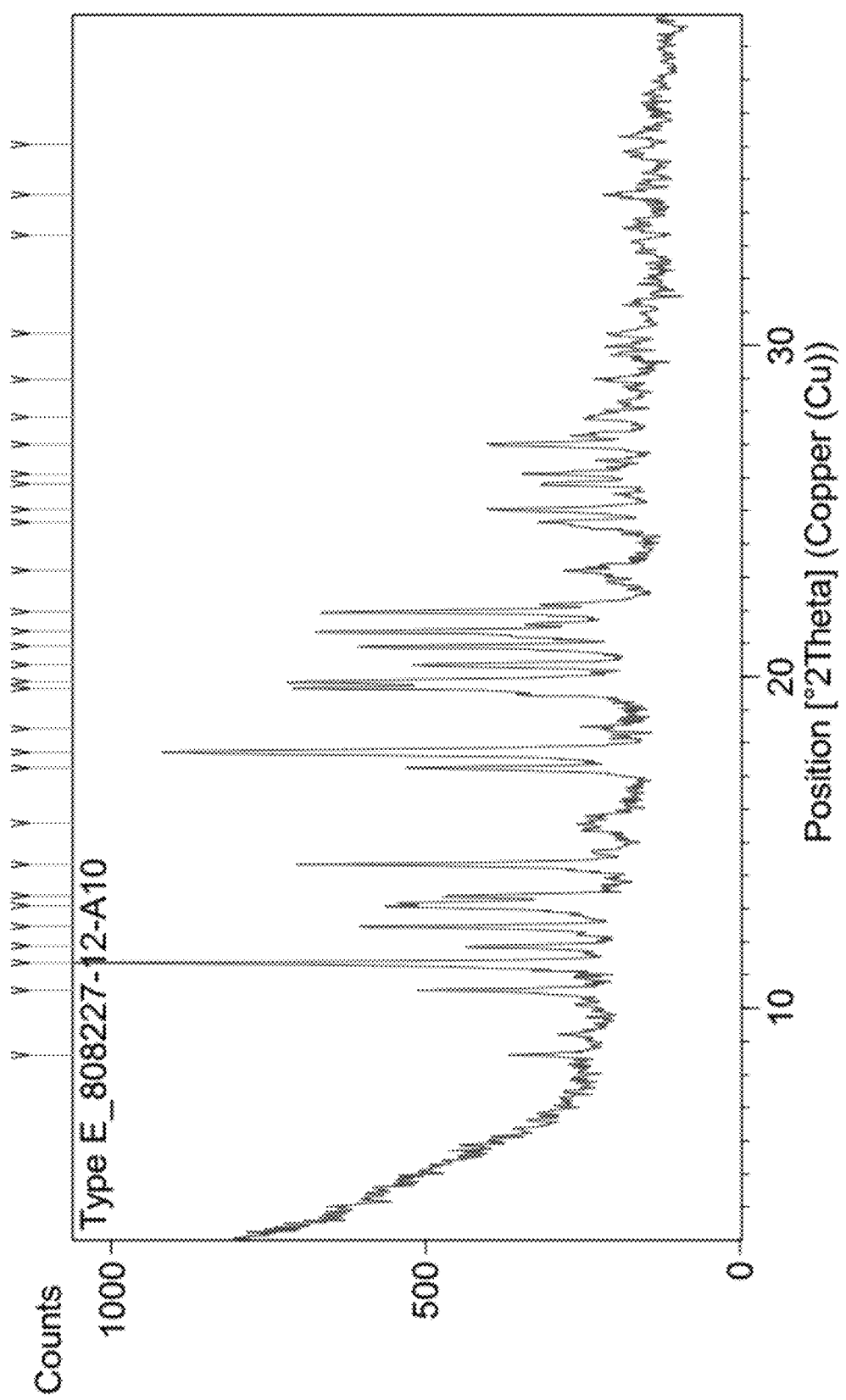
FIG. 5 shows an embodiment of XRPD pattern of Form E of BBR-UDCA.

In certain embodiments, the solid form (Form E of BBR-UDCA) is characterized by an X-ray powder diffraction (XRPD) pattern comprising peaks at diffraction angles 2θ essentially the same as the one presented in FIG. 5.

In certain embodiments, the solid form (Form E of BBR-UDCA) is characterized by a purity of 70% or higher.

In certain embodiments, the solid form (Form E of BBR-UDCA) is characterized by a purity of 95% or higher.

In yet another aspect, the invention generally relates to a solid form, which is Form H of BBR-UDCA, having an X-ray powder diffraction (XRPD) pattern comprising one or more peaks at 2θ values selected from the group consisting of: 13.05, 14.63 and 25.46° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form H of BBR-UDCA) has an X-ray powder diffraction (XRPD) pattern comprising peaks at 2θ values of 13.05, 14.63 and 25.46° (±0.2°).

In certain embodiments, the solid form (Form H of BBR-UDCA) is a hydrate of berberine ursodeoxycholate.

Figure 6:
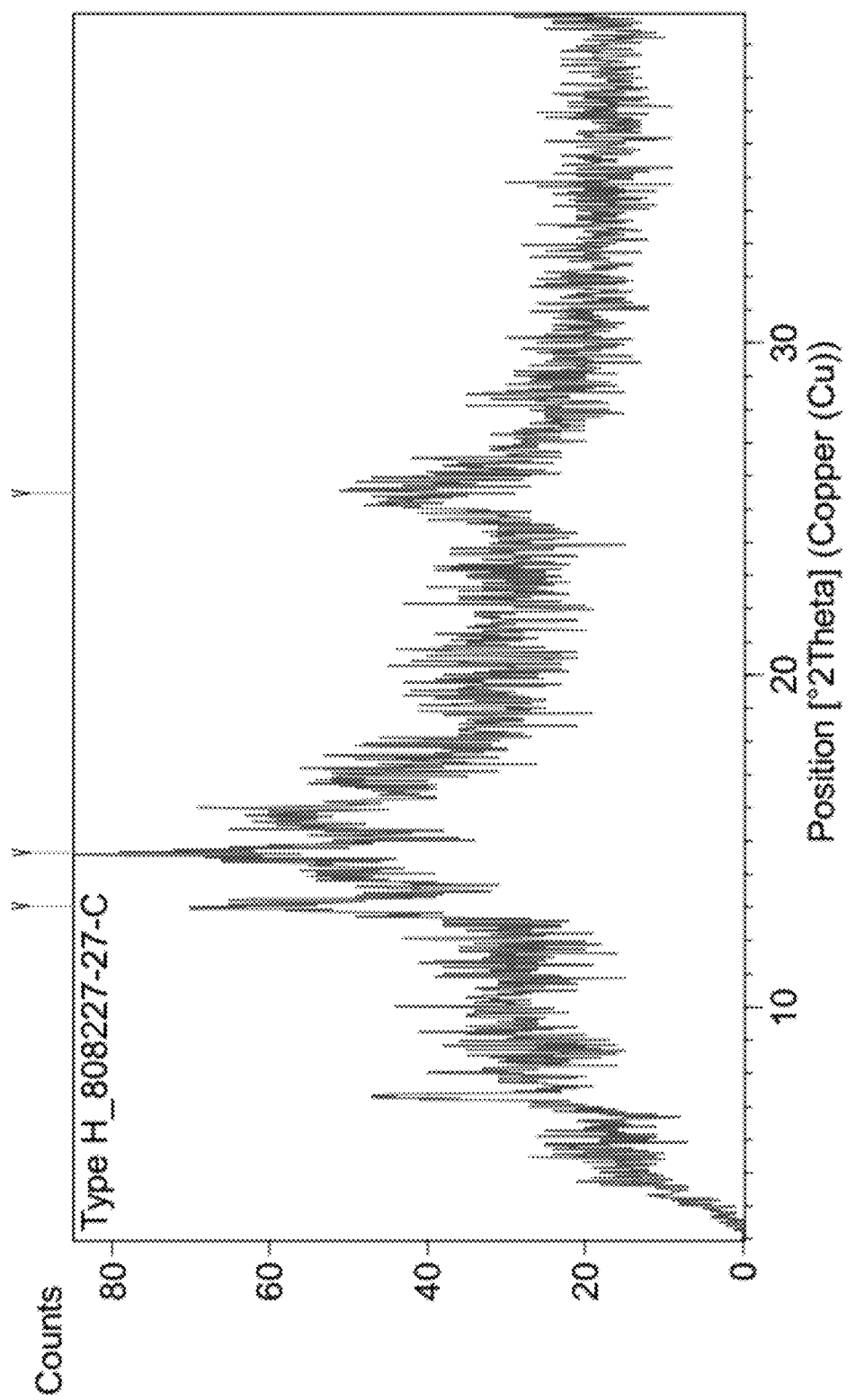
FIG. 6 shows an embodiment of XRPD pattern of Form H of BBR-UDCA.

In certain embodiments, the solid form (Form H of BBR-UDCA) is characterized by an X-ray powder diffraction (XRPD) pattern comprising peaks at diffraction angles 2θ essentially the same as the one presented in FIG. 6.

In certain embodiments, the solid form (Form H of BBR-UDCA) is characterized by a differential scanning calorimetry (DSC) curve comprising an endotherm at about 97.1° C. (peak temperature) and an endotherm at about 138.3° C. (onset temperature).

Figure 23:
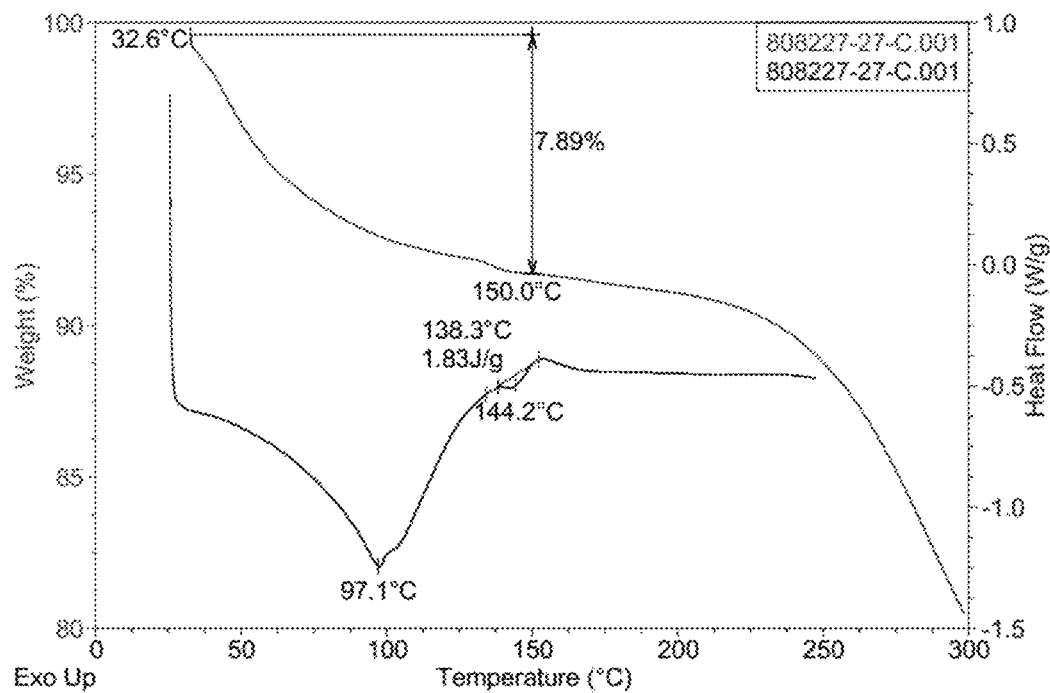
FIG. 23 shows an embodiment of a TGA/DSC graph of Form H of BBR-UDCA.

In certain embodiments, the solid form (Form H of BBR-UDCA) is characterized by a differential scanning calorimetry (DSC) curve essentially the same as the one presented in FIG. 23.

In certain embodiments, the solid form (Form H of BBR-UDCA) is characterized by a purity of 70% or higher.

In certain embodiments, the solid form (Form H of BBR-UDCA) is characterized by a purity of 95% or higher.

In yet another aspect, the invention generally relates to a solid form, which is Form I of BBR-UDCA, having an X-ray powder diffraction (XRPD) pattern comprising one or more peaks at 2θ values selected from the group consisting of: 4.19, 7.64, 10.03, 13.32, 13.84, 14.83, 16.73, 22.73, 25.61 and 28.57° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form I of BBR-UDCA) has an X-ray powder diffraction (XRPD) pattern comprising peaks at 2θ values of 7.64, 10.03, 13.32, 16.73 and 22.73° (±0.2°).

In certain embodiments, the solid form (Form I of BBR-UDCA) has an X-ray powder diffraction (XRPD) pattern comprising peaks at 2θ values of 4.19, 7.64, 10.03, 13.32, 13.84, 14.83, 16.73, 22.73, 25.61 and 28.57° (±0.2°).

In certain embodiments, the solid form (Form I of BBR-UDCA) is a hydrate of berberine ursodeoxycholate.

Figure 7:
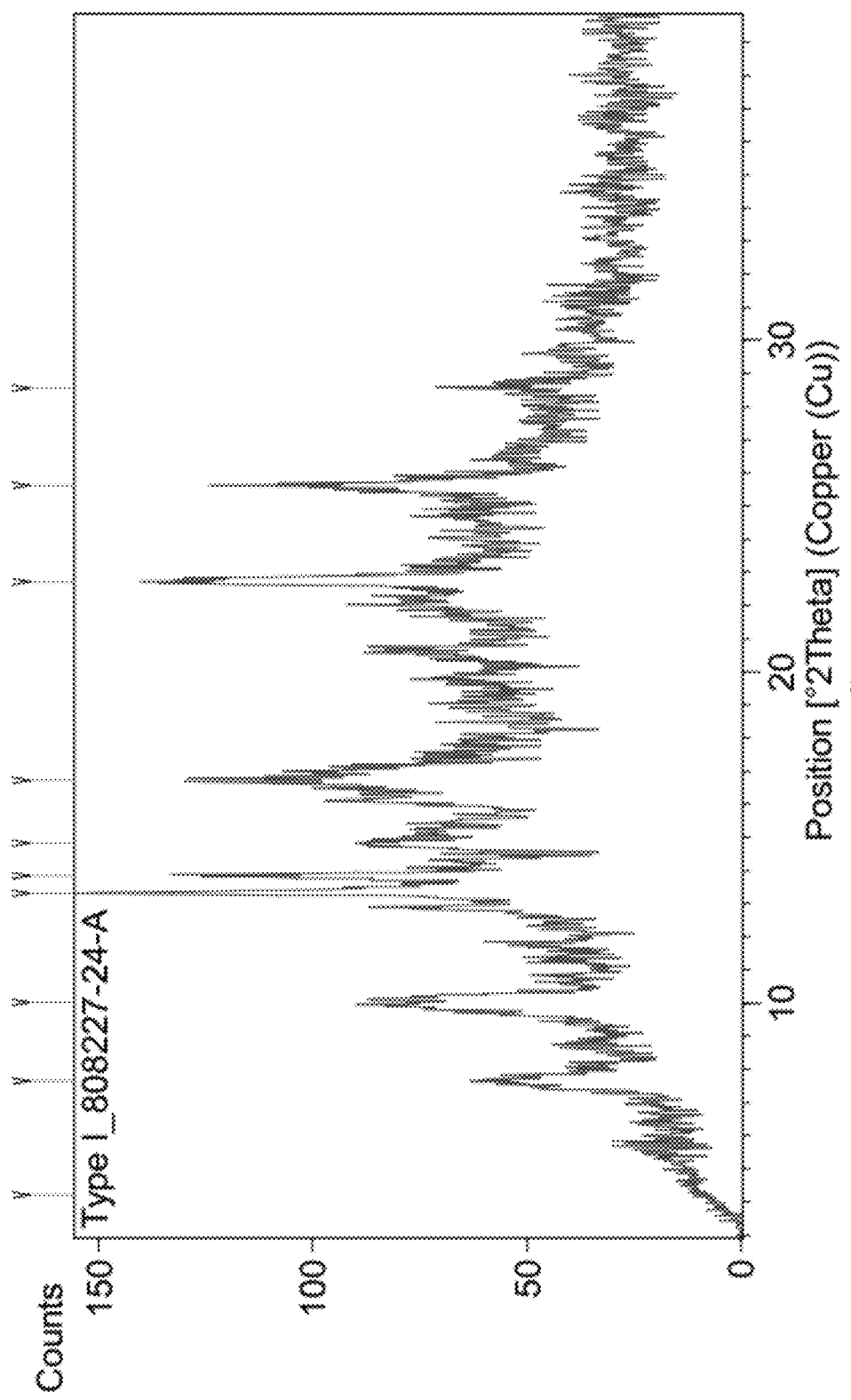
FIG. 7 shows an embodiment of XRPD pattern of Form I of BBR-UDCA.

In certain embodiments, the solid form (Form I of BBR-UDCA) is characterized by an X-ray powder diffraction (XRPD) pattern comprising peaks at diffraction angles 2θ essentially the same as the one presented in FIG. 7.

In certain embodiments, the solid form (Form I of BBR-UDCA) is characterized by a differential scanning calorimetry (DSC) curve comprising an endotherm at about 56.2° C. (onset temperature) and an endotherm at about 79.6° C. (onset temperature).

Figure 24:
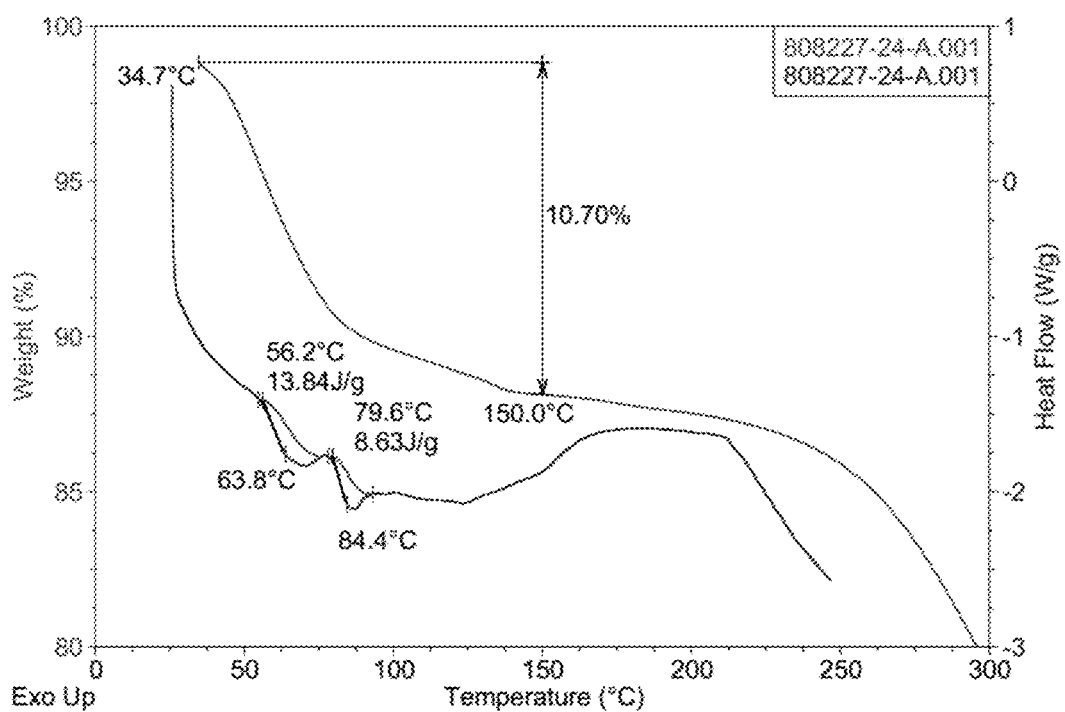
FIG. 24 shows an embodiment of a TGA/DSC graph of Form I of BBR-UDCA.

In certain embodiments, the solid form (Form I of BBR-UDCA) is characterized by a differential scanning calorimetry (DSC) curve essentially the same as the one presented in FIG. 24.

In certain embodiments, the solid form (Form I of BBR-UDCA) is characterized by a purity of 70% or higher.

In certain embodiments, the solid form (Form I of BBR-UDCA) is characterized by a purity of 95% or higher.

In yet another aspect, the invention generally relates to a solid form, which is Form J of BBR-UDCA, having an X-ray powder diffraction (XRPD) pattern comprising one or more peaks at 2θ values selected from the group consisting of: 4.61, 6.32, 7.38, 8.22, 9.21, 10.57, 11.73, 12.13, 12.62, 12.96, 13.87, 14.55, 14.78, 15.81, 16.48, 17.69, 18.39, 19.01, 20.06, 21.25, 22.13, 23.20, 24.47, 24.89, 26.31, 27.98, 30.25 and 33.35° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form J of BBR-UDCA) has an X-ray powder diffraction (XRPD) pattern comprising peaks at 2θ values of 4.61, 10.57, 14.78, 19.01 and 26.31° (±0.2°).

In certain embodiments, the solid form (Form J of BBR-UDCA) has an X-ray powder diffraction (XRPD) pattern comprising peaks at 2θ values of 4.61, 7.38, 8.22, 9.21, 10.57, 14.55, 14.78, 16.48, 17.69, 19.01, 20.06, 24.47 and 26.31° (±0.2°).

In certain embodiments, the solid form (Form J of BBR-UDCA) has an X-ray powder diffraction (XRPD) pattern comprising peaks at 2θ values of 4.61, 6.32, 7.38, 8.22, 9.21, 10.57, 11.73, 12.13, 12.62, 12.96, 13.87, 14.55, 14.78, 15.81, 16.48, 17.69, 18.39, 19.01, 20.06, 21.25, 22.13, 23.20, 24.47, 24.89, 26.31, 27.98, 30.25 and 33.35° (±0.2°).

In certain embodiments, the solid form (Form J of BBR-UDCA) is an anhydrous berberine ursodeoxycholate.

Figure 8:
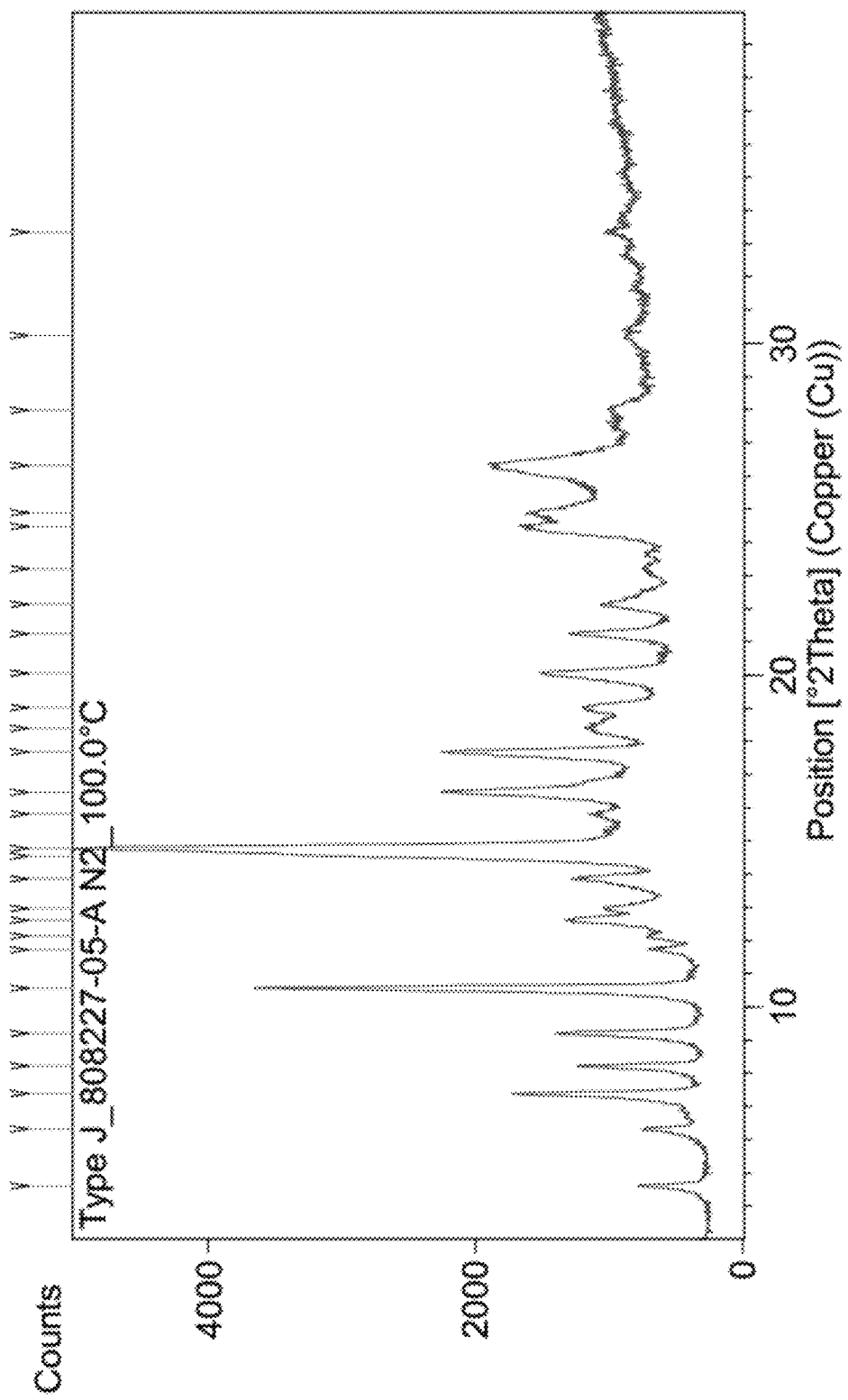
FIG. 8 shows an embodiment of XRPD pattern of Form J of BBR-UDCA.

In certain embodiments, the solid form (Form J of BBR-UDCA) is characterized by an X-ray powder diffraction (XRPD) pattern comprising peaks at diffraction angles 2θ essentially the same as the one presented in FIG. 8.

In certain embodiments, the solid form (Form J of BBR-UDCA) is characterized by a purity of 70% or higher.

In certain embodiments, the solid form (Form J of BBR-UDCA) is characterized by a purity of 95% or higher.

In yet another aspect, the invention generally relates to a solid form, which is Form P of BBR-UDCA, having an X-ray powder diffraction (XRPD) pattern comprising one or more peaks at 2θ values selected from the group consisting of: 3.11, 5.01, 5.78, 7.26, 9.20, 10.10, 10.79, 11.65, 13.70, 14.59, 15.22, 16.19, 16.54, 17.05, 18.06, 18.68, 20.52, 21.09, 21.73, 22.49, 24.73, 25.42, 25.94 and 30.11° (±0.2°) obtained using Cu Kα radiation ($\lambda_1$=1.540598 Å, $\lambda_2$=1.544426 Å, intensity ratio $\lambda_2/\lambda_1$=0.50)

In certain embodiments, the solid form (Form P of BBR-UDCA) has an X-ray powder diffraction (XRPD) pattern comprising peaks at 2θ values of 5.01, 5.78, 11.65, 17.05, 18.68 and 20.52° (±0.2°).

In certain embodiments, the solid form (Form P of BBR-UDCA) has an X-ray powder diffraction (XRPD) pattern comprising peaks at 2θ values of 5.01, 5.78, 7.26, 9.20, 10.10, 10.79, 11.65, 13.70, 14.59, 15.22, 16.19, 16.54, 17.05, 18.68, 20.52 and 25.94° (±0.2°).

In certain embodiments, the solid form (Form P of BBR-UDCA) has an X-ray powder diffraction (XRPD) pattern comprising peaks at 2θ values of 3.11, 5.01, 5.78, 7.26, 9.20, 10.10, 10.79, 11.65, 13.70, 14.59, 15.22, 16.19, 16.54, 17.05, 18.06, 18.68, 20.52, 21.09, 21.73, 22.49, 24.73, 25.42, 25.94 and 30.11° (±0.2°).

In certain embodiments, the solid form (Form P of BBR-UDCA) is a hydrate of berberine ursodeoxycholate.

Figure 9:
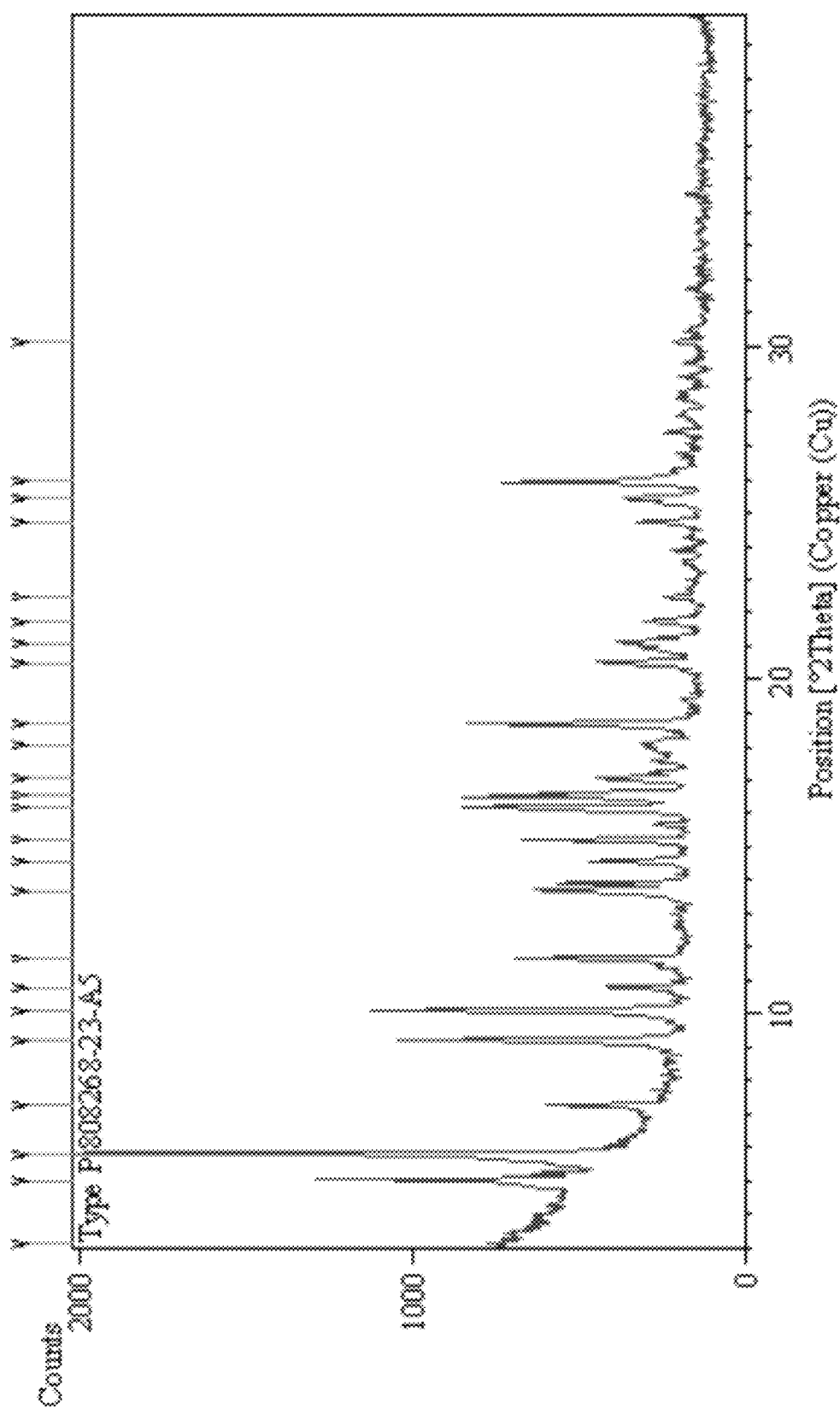
FIG. 9 shows an embodiment of XRPD pattern of Form P of BBR-UDCA.

In certain embodiments, the solid form (Form P of BBR-UDCA) is characterized by an X-ray powder diffraction (XRPD) pattern comprising peaks at diffraction angles 2θ essentially the same as the one presented in FIG. 9.

In certain embodiments, the solid form (Form P of BBR-UDCA) is characterized by a differential scanning calorimetry (DSC) curve comprising an endotherm at about 100.3° C. (peak temperature), an endotherm at about 122.5° C. (peak temperature) and an endotherm at about 168.7° C. (peak temperature).

Figure 25:
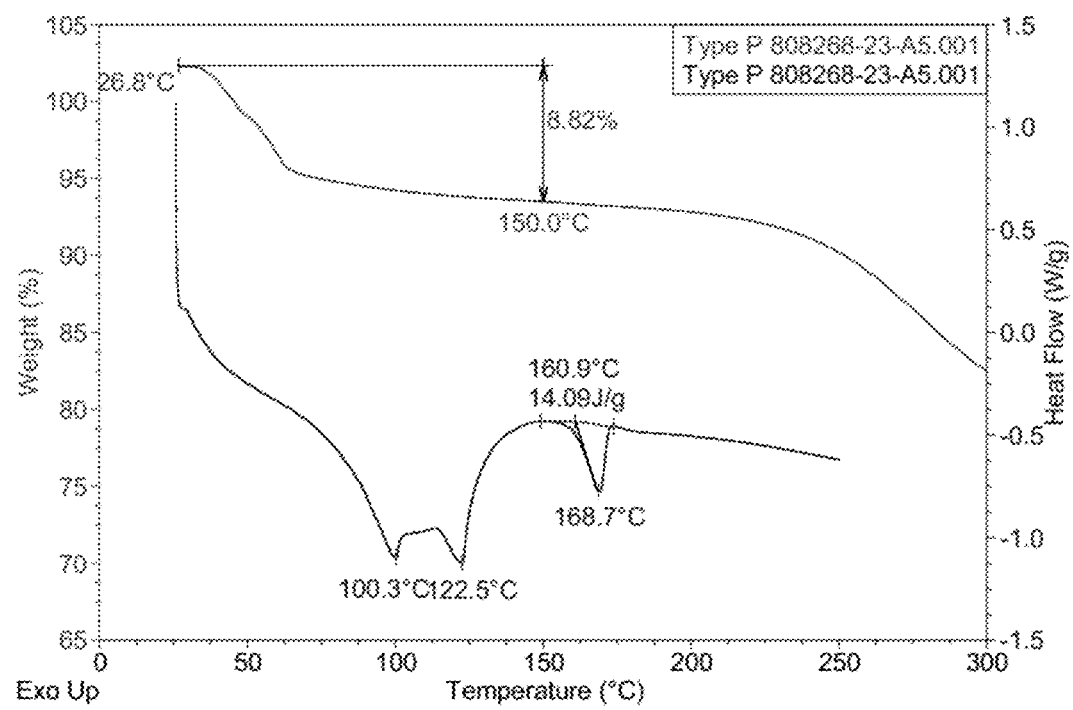
FIG. 25 shows an embodiment of a TGA/DSC graph of Form P of BBR-UDCA.

In certain embodiments, the solid form (Form P of BBR-UDCA) is characterized by a differential scanning calorimetry (DSC) curve essentially the same as the one presented in FIG. 25.

In certain embodiments, the solid form (Form P of BBR-UDCA) is characterized by a purity of 70% or higher.

In certain embodiments, the solid form (Form P of BBR-UDCA) is characterized by a purity of 95% or higher.

In yet another aspect, the invention generally relates to a solid form, which is Form W of BBR-UDCA, having an X-ray powder diffraction (XRPD) pattern comprising one or more peaks at 2θ values selected from the group consisting of: 6.49, 7.16, 8.51, 10.21, 12.01, 13.13, 13.90, 14.42, 15.18, 15.57, 16.03, 16.45, 16.74, 17.08, 17.85, 18.39, 19.61, 20.43, 21.39, 21.70, 23.51 and 25.21° (±0.2°) obtained using Cu Kα radiation ($\lambda_1$=1.540598 Å, $\lambda_2$=1.544426 Å, intensity ratio $\lambda_2/\lambda_1$=0.50).

In certain embodiments, the solid form (Form W of BBR-UDCA) has an X-ray powder diffraction (XRPD) pattern comprising peaks at 2θ values of 6.49, 7.16, 12.01, 13.13, 15.18, 16.45, 17.85, 21.39 and 25.21° (±0.2°).

In certain embodiments, the solid form (Form W of BBR-UDCA) has an X-ray powder diffraction (XRPD) pattern comprising peaks at 2θ values of 6.49, 7.16, 8.51, 10.21, 12.01, 13.13, 13.90, 14.42, 15.18, 15.57, 16.03, 16.45, 16.74, 17.08, 17.85, 18.39, 19.61, 20.43, 21.39, 21.70, 23.51 and 25.21° (±0.2°).

In certain embodiments, the solid form (Form W of BBR-UDCA) is a hydrate of berberine ursodeoxycholate.

Figure 10:
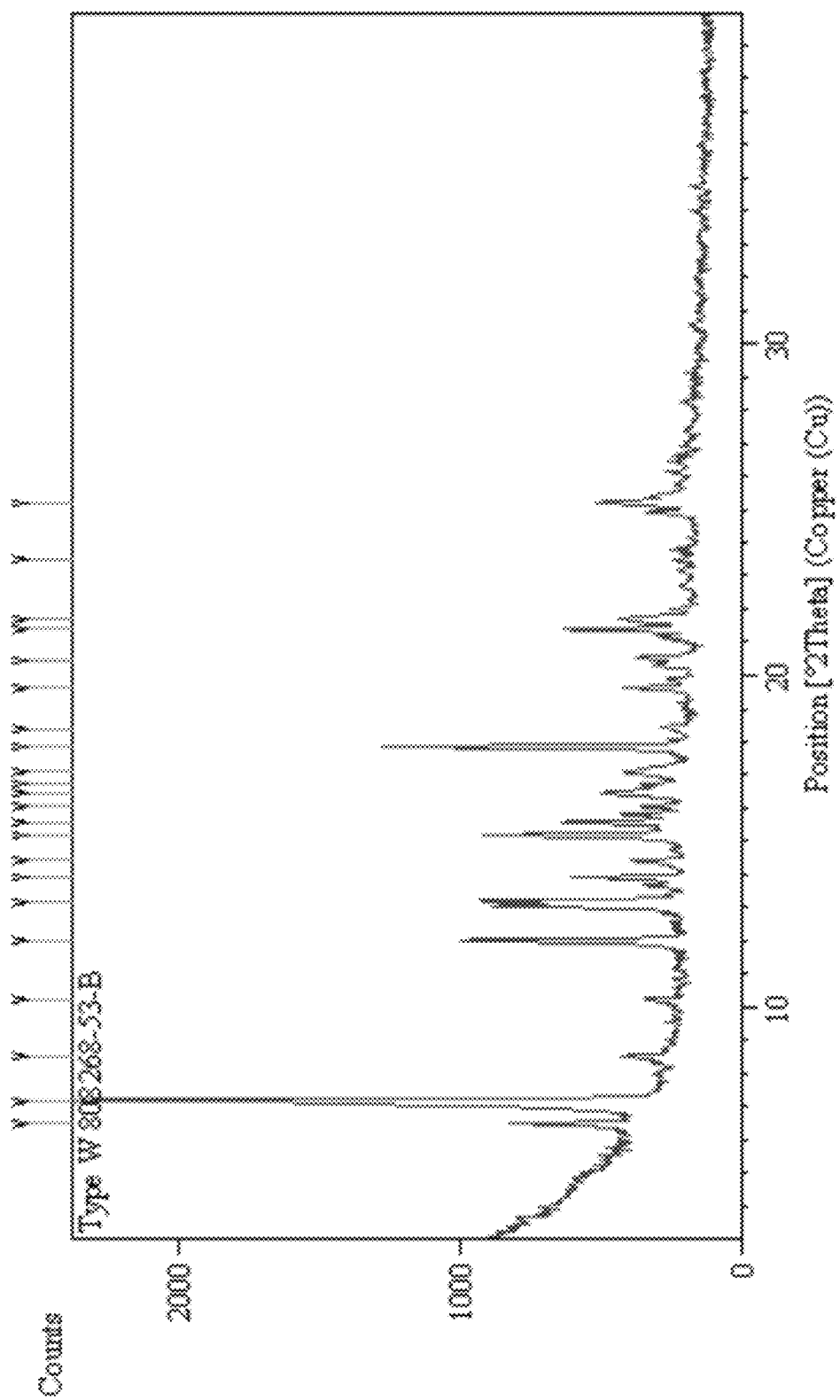
FIG. 10 shows an embodiment of XRPD pattern of Form W of BBR-UDCA.

In certain embodiments, the solid form (Form W of BBR-UDCA) is characterized by an X-ray powder diffraction (XRPD) pattern comprising peaks at diffraction angles 2θ essentially the same as the one presented in FIG. 10.

In certain embodiments, the solid form (Form W of BBR-UDCA) is characterized by a differential scanning calorimetry (DSC) curve comprising an endotherm at about 82.1° C. (peak temperature) and an endotherm at about 106.4° C. (peak temperature).

Figure 26:
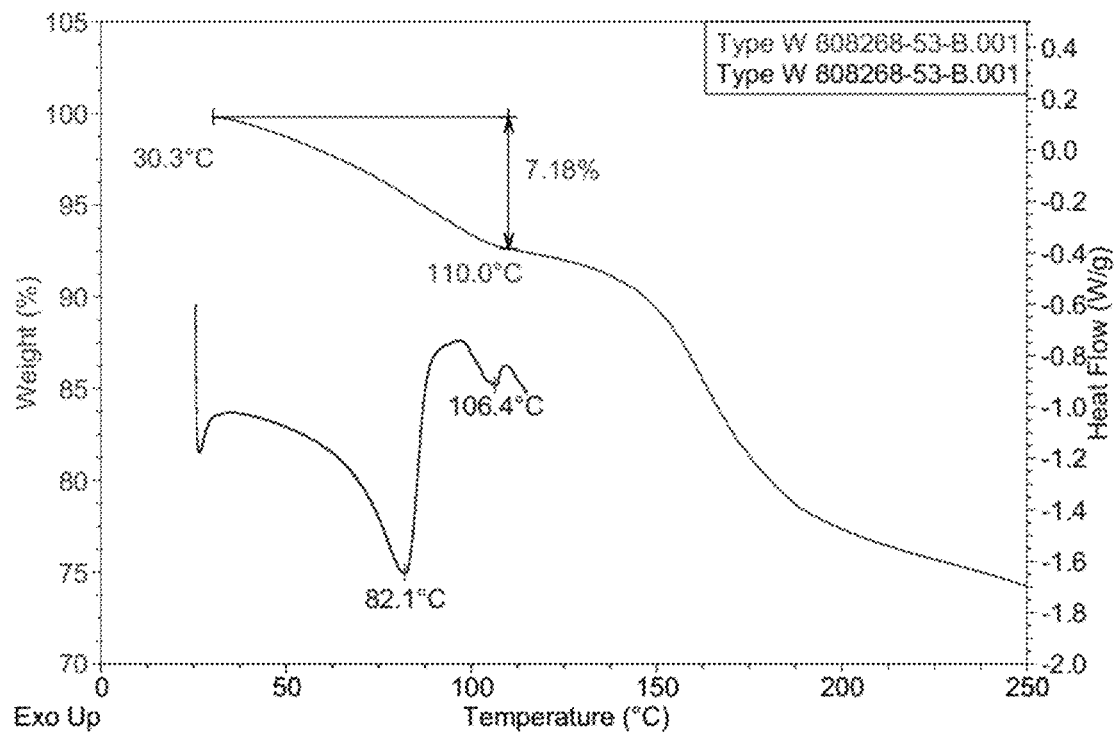
FIG. 26 shows an embodiment of a TGA/DSC graph of Form W of BBR-UDCA.

In certain embodiments, the solid form (Form W of BBR-UDCA) is characterized by a differential scanning calorimetry (DSC) curve essentially the same as the one presented in FIG. 26.

In certain embodiments, the solid form (Form W of BBR-UDCA) is characterized by a purity of 70% or higher.

In certain embodiments, the solid form (Form W of BBR-UDCA) is characterized by a purity of 95% or higher.

In yet another aspect, the invention generally relates to a solid form, which is Form X of BBR-UDCA, having an X-ray powder diffraction (XRPD) pattern comprising one or more peaks at 2θ values selected from the group consisting of: 3.63, 6.61, 7.24, 10.49, 11.95, 13.51, 14.26, 14.54, 15.14, 16.01, 16.82, 18.28, 20.26, 21.08, 21.49, 21.90, 25.60, 26.40, 27.31, 29.34, 30.59, 31.01, 34.04, 34.68 and 36.91° (±0.2°) obtained using Cu Kα radiation of ($\lambda_1$=1.540598 Å, $\lambda_2$=1.544426 Å, intensity ratio $\lambda_2/\lambda_1$=0.50).

In certain embodiments, the solid form (Form X of BBR-UDCA) has an X-ray powder diffraction (XRPD) pattern comprising peaks at 2θ values of 3.63, 7.24, 11.95, 13.51, 14.54, 15.14, 18.28, 21.90 and 25.60° (±0.2°).

In certain embodiments, the solid form (Form X of BBR-UDCA) has an X-ray powder diffraction (XRPD) pattern comprising peaks at 2θ values of 3.63, 6.61, 7.24, 10.49, 11.95, 13.51, 14.26, 14.54, 15.14, 16.01, 16.82, 18.28, 20.26, 21.08, 21.49, 21.90, 25.60, 26.40, 27.31, 29.34, 30.59, 31.01, 34.04, 34.68 and 36.91° (±0.2°).

In certain embodiments, the solid form (Form X of BBR-UDCA) is a hydrate of berberine ursodeoxycholate.

Figure 11:
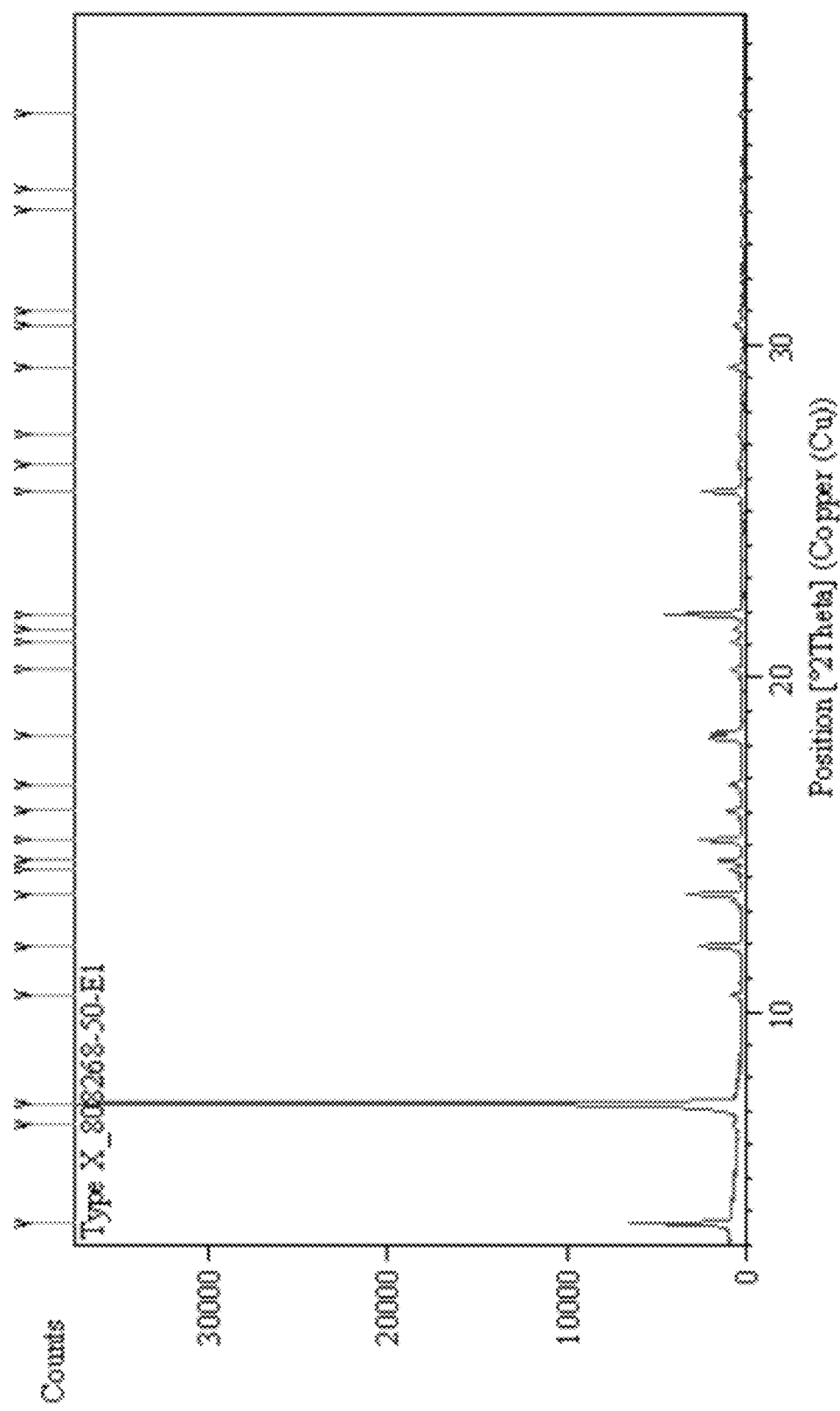
FIG. 11 shows an embodiment of XRPD pattern of Form X of BBR-UDCA.

In certain embodiments, the solid form (Form X of BBR-UDCA) is characterized by an X-ray powder diffraction (XRPD) pattern comprising peaks at diffraction angles 2θ essentially the same as the one presented in FIG. 11.

In certain embodiments, the solid form (Form X of BBR-UDCA) is characterized by a differential scanning calorimetry (DSC) curve comprising an endotherm at about 86.7° C. (peak temperature) and an endotherm at about 189.1° C. (peak temperature).

Figure 27:
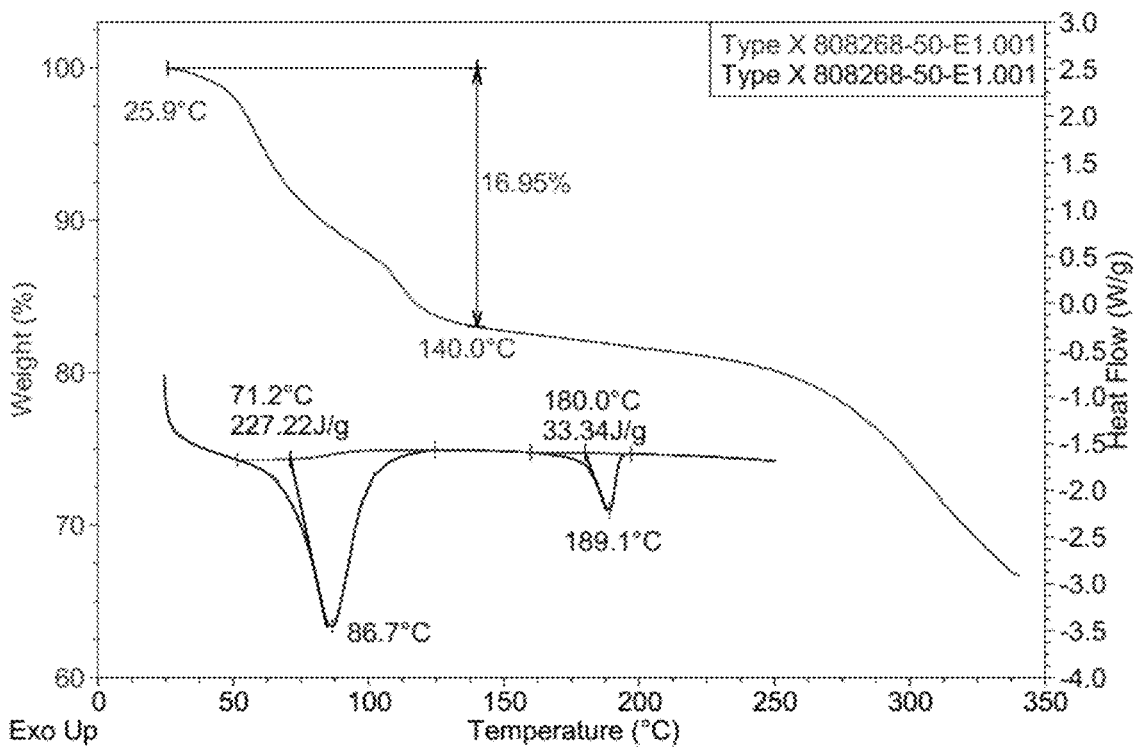
FIG. 27 shows an embodiment of a TGA/DSC graph of Form X of BBR-UDCA.

In certain embodiments, the solid form (Form X of BBR-UDCA) is characterized by a differential scanning calorimetry (DSC) curve essentially the same as the one presented in FIG. 27.

In certain embodiments, the solid form (Form X of BBR-UDCA) is characterized by a purity of 70% or higher.

In certain embodiments, the solid form (Form X of BBR-UDCA) is characterized by a purity of 95% or higher.

In yet another aspect, the invention generally relates to a solid form of hemi-nonahydrate of berberine ursodeoxycholate.

In yet another aspect, the invention generally relates to a composition comprising one or more solid forms disclosed herein (e.g., one or more of Forms A, B, C, D, E, H, I, J, P, W, and X).

In yet another aspect, the invention generally relates to a composition comprising two or more solid forms disclosed herein (e.g., two or more of Forms A, B, C, D, E, H, I, J, P, W, and X).

The composition of comprising one or more (or two or more) solid forms disclosed herein may include further agents as needed.

In certain embodiments, the composition further includes, in addition to berberine ursodeoxycholate, one or more other therapeutically effective agents.

In certain embodiments, the composition further includes one or more agents selected from the group consisting of vitamin D, vitamin C, vitamin E, vitamin B12, vitamin A, benfotiamine, chromium picolinate and vanadium.

In certain embodiments, the composition further includes one or more agents selected from the group consisting of omega-3 fatty acids, S-adenosylmethionine, N-acetyl cysteine, silymarin, polyenylphosphatidylcholine, and resveratrol.

In yet another aspect, the invention generally relates to a pharmaceutical composition comprising Form A of BBR-UDCA and a pharmaceutically acceptable excipient, carrier, or diluent.

In yet another aspect, the invention generally relates to a pharmaceutical composition comprising Form B of BBR-UDCA and a pharmaceutically acceptable excipient, carrier, or diluent.

In yet another aspect, the invention generally relates to a pharmaceutical composition comprising Form C of BBR-UDCA and a pharmaceutically acceptable excipient, carrier, or diluent.

In yet another aspect, the invention generally relates to a pharmaceutical composition comprising Form D of BBR-UDCA and a pharmaceutically acceptable excipient, carrier, or diluent.

In yet another aspect, the invention generally relates to a pharmaceutical composition comprising Form E of BBR-UDCA and a pharmaceutically acceptable excipient, carrier, or diluent.

In yet another aspect, the invention generally relates to a pharmaceutical composition comprising Form H of BBR-UDCA and a pharmaceutically acceptable excipient, carrier, or diluent.

In yet another aspect, the invention generally relates to a pharmaceutical composition comprising Form I of BBR-UDCA and a pharmaceutically acceptable excipient, carrier, or diluent.

In yet another aspect, the invention generally relates to a pharmaceutical composition comprising Form J of BBR-UDCA and a pharmaceutically acceptable excipient, carrier, or diluent.

In yet another aspect, the invention generally relates to a pharmaceutical composition comprising Form P of BBR-UDCA and a pharmaceutically acceptable excipient, carrier, or diluent.

In yet another aspect, the invention generally relates to a pharmaceutical composition comprising Form W of BBR-UDCA and a pharmaceutically acceptable excipient, carrier, or diluent.

In yet another aspect, the invention generally relates to a pharmaceutical composition comprising Form X of BBR-UDCA and a pharmaceutically acceptable excipient, carrier, or diluent.

In certain embodiments, the pharmaceutical composition comprising one or more solid forms disclosed herein (e.g., one or more of Forms A, B, C, D, E, H, I, J, P, W, and X).

In certain embodiments, the pharmaceutical composition comprising two or more solid forms disclosed herein (e.g., two or more of Forms A, B, C, D, E, H, I, J, P, W, and X).

In certain embodiments, the pharmaceutical composition further includes, in addition to berberine ursodeoxycholate, one or more other therapeutically effective agents.

In certain embodiments, the pharmaceutical composition of the invention further includes one or more agents selected from the group consisting of vitamin D, vitamin C, vitamin E, vitamin B12, vitamin A, benfotiamine, chromium picolinate and vanadium.

In certain embodiments, the pharmaceutical composition of the invention further includes one or more agents selected from the group consisting of omega-3 fatty acids, S-adenosylmethionine, N-acetyl cysteine, silymarin, polyenylphosphatidylcholine, and resveratrol.

In yet another aspect, the invention generally relates to a unit dosage form comprising a pharmaceutical composition disclosed herein.

In certain embodiments, the unit dosage form is an oral dosage form.

Any suitable dosage forms may be utilized. In certain embodiments, the unit dosage form is a tablet. In certain embodiments, the unit dosage form is a capsule. In certain embodiments, the unit dosage form is a certain volume of suspension.

In certain embodiments, the invention provides a tablet comprising any of the solid forms of BBR-UDCA or pharmaceutical compositions disclosed herein. For example, in one embodiment the tablet comprises from about 1 to about 1,000 mg of a solid form of BBR-UDCA (e.g., one or more of Forms A, B, C, D, E, H, I, J, P, W, and X). Further, for example, the tablet comprises from about 50 to about 500 mg of a solid form of BBR-UDCA (e.g., one or more of Forms A, B, C, D, E, H, I, J, P, W, and X). Even further, for example, the tablet comprises about 500 to 1,000 mg of a solid form of BBR-UDCA (e.g., one or more of Forms A, B, C, D, E, H, I, J, P, W, and X). Even further, for example, the tablet comprises about 50 mg, about 100 mg, about 150 mg, about 200 mg, about 250 mg, about 300 mg, about 350 mg, or about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg of a solid form of BBR-UDCA (e.g., one or more of Forms A, B, C, D, E, H, I, J, P, W, and X).

In certain embodiments, the invention provides a soft gelatin capsule comprising any of the solid forms of BBR-UDCA or pharmaceutical compositions disclosed herein. For example, in one embodiment the soft gelatin capsule comprises from about 1 to about 1,000 mg of a solid form of BBR-UDCA (e.g., one or more of Forms A, B, C, D, E, H, I, J, P, W, and X). Further, for example, the soft gelatin capsule comprises from about 50 to about 500 mg of a solid form of BBR-UDCA (e.g., one or more of Forms A, B, C, D, E, H, I, J, P, W, and X). Even further, for example, the soft gelatin capsule comprises about 500 to 1,000 mg of a solid form of BBR-UDCA (e.g., one or more of Forms A, B, C, D, E, H, I, J, P, W, and X). Even further, for example, the soft gelatin capsule comprises about 50 mg, about 100 mg, about 150 mg, about 200 mg, about 250 mg, about 300 mg, about 350 mg, or about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg of a solid form of BBR-UDCA (e.g., one or more of Forms A, B, C, D, E, H, I, J, P, W, and X).

In yet another aspect, the invention generally relates to a method for treating, reducing, or preventing a metabolic disorder, a heart disease, a neurodegenerative disease, or a liver disease, comprising administering to a subject in need thereof a therapeutically effective amount of a pharmaceutical composition disclosed herein.

In yet another aspect, the invention generally relates to a method for treating, reducing, or preventing a disease or disorder, comprising administering to a subject in need thereof a therapeutically effective amount of a pharmaceutical composition disclosed herein or a unit dosage form disclosed herein, effective to treat, prevent, or reduce one or more diseases or disorders selected from fatty liver, non-alcoholic fatty liver disease (NAFLD) and non-alcoholic steatohepatitis (NASH), cholestatic liver diseases, graft-versus-host disease of the liver, primary sclerosing cholangitis, chronic viral associated liver diseases, alcohol-related liver diseases, metabolic diseases or disorders such as pre-diabetes, diabetes, hyperlipidemia, hypercholesterolemia, diabetic dyslipidemia, dyslipidemia in statin-intolerant patients, obesity, or a related disease or disorder thereof in a mammal, including a human.

In certain embodiments, the disease or disorder is cholestatic liver diseases, graft-versus-host disease of the liver, chronic viral associated liver diseases or alcohol-related liver diseases, or a related disease or disorder.

In certain embodiments, the disease or disorder is fatty liver, NAFLD or NASH, or a related disease or disorder.

In certain embodiments, the disease or disorder is NAFLD, or a related disease or disorder.

In certain embodiments, the disease or disorder is NASH, or a related disease or disorder.

In certain embodiments, the disease or disorder is primary sclerosing cholangitis, or a related disease or disorder.

In certain embodiments, the disease or disorder is hypercholesterolemia, or a related disease or disorder.

In certain embodiments, the disease or disorder is pre-diabetes, diabetes or hyperlipidemia, diabetic dyslipidemia, or dyslipidemia, or a related disease or disorder, in statin-intolerant patients.

In certain embodiments, the disease or disorder is obesity, or a related disease or disorder.

In certain embodiments, the subject is administered, in addition to berberine ursodeoxycholate, one or more other therapeutically effective agents.

In certain embodiments, the invention relates to a solid form of BBR-UDCA, wherein the solid form is non-hygroscopic.

In certain embodiments, the invention relates to a solid form of BBR-UDCA, wherein the solid form is anhydrous.

In certain embodiments, the invention relates to a solid form of BBR-UDCA, wherein the solid form comprises a plurality of small crystallites of BBR-UDCA.

In yet another aspect, the invention generally relates to a method for preparing Form A of berberine ursodeoxycholate. The method includes: forming a mixture of a crystalline and/or amorphous form of berberine ursodeoxycholate with co-solvents of an organic solvent and $H_2O$, wherein the water activity is greater than about 0.4; stirring the mixture at room temperature, filtering the mixture to obtain a filter cake; washing the filter cake with distilled water; and removing water to obtain Form A of berberine ursodeoxycholate.

In certain embodiments, the organic solvent is EtOH.

In certain embodiments, the EtOH:$H_2O$ (v/v) is from about 1:5 to about 1:30. In certain embodiments, the EtOH:$H_2O$ (v/v) is from about 1:10 to about 1:20. In certain embodiments, the EtOH:$H_2O$ (v/v) is about 1:10.

In certain embodiments, the mixture is stirred at room temperature for about 1 to about 24 hours. In certain embodiments, the mixture is stirred at room temperature for about 2 to about 7 hours. In certain embodiments, the mixture is stirred at room temperature for about 3 to about 5 hours.

In certain embodiments, removing water until the water content is about 10% or less to obtain Form A of berberine ursodeoxycholate.

In yet another aspect, the invention generally relates to a method for preparing Form B of berberine ursodeoxycholate. The method includes: forming a mixture of a crystalline and/or amorphous form of berberine ursodeoxycholate with acetonitrile/$H_2O$, wherein the acetonitrile:$H_2O$ (v/v) is from about 1:2 to about 2:1; and slowly evaporating to remove acetonitrile/$H_2O$ to obtain Form B of berberine ursodeoxycholate.

In certain embodiments, the acetonitrile:$H_2O$ (v/v) is about 1:1.

In yet another aspect, the invention generally relates to a method for preparing Form C of berberine ursodeoxycholate. The method includes: forming a mixture of a crystalline and/or amorphous form of berberine ursodeoxycholate with isopropyl alcohol/isopropyl acetate, wherein the isopropyl alcohol:isopropyl acetate (v/v) is from about 1:2 to about 2:1; and slowly evaporating to remove isopropyl alcohol/isopropyl acetate to obtain Form C of berberine ursodeoxycholate.

In certain embodiments, the isopropyl alcohol:isopropyl acetate (v/v) is about 1:1.

In yet another aspect, the invention generally relates to a method for preparing Form D of berberine ursodeoxycholate. The method includes: forming a mixture of crystalline and/or amorphous form of berberine ursodeoxycholate with an organic solvent or an organic solvent/water co-solvents having a water activity less than about 0.2; stirring the mixture at room temperature; and filtering the mixture to obtain Form D of berberine ursodeoxycholate.

In certain embodiments, a mixture of crystalline and/or amorphous form of berberine ursodeoxycholate with ethyl acetate is formed.

In certain embodiments, the mixture is stirred at room temperature for about 1 to about 24 hours. In certain embodiments, the mixture is stirred at room temperature for about 2 to about 7 hours. In certain embodiments, the mixture is stirred at room temperature for about 3 to about 5 hours.

In yet another aspect, the invention generally relates to a method for preparing Form E of berberine ursodeoxycholate. The method includes: providing Form A of berberine ursodeoxycholate; and performing solid vapor diffusion in a dichloromethane atmosphere to obtain Form E of berberine ursodeoxycholate.

In yet another aspect, the invention generally relates to a method for preparing Form H of berberine ursodeoxycholate. The method includes: dissolving a crystalline and/or amorphous form of berberine ursodeoxycholate in acetonitrile/$H_2O$, wherein the acetonitrile: $H_2O$ (v/v) is from about 1:2 to about 2:1; slowly evaporating acetonitrile/$H_2O$; collecting precipitate by filtration; heating the obtained precipitate to about 100° C.; and cooling heated precipitate to room temperature to obtain Form H of berberine ursodeoxycholate.

In certain embodiments, the acetonitrile:$H_2O$ (v/v) is about 1:1.

In certain embodiments, the obtained precipitate is heated for about 0.5 to about 2 hours.

In yet another aspect, the invention generally relates to a method for preparing Form I of berberine ursodeoxycholate. The method includes: dissolving a crystalline and/or amorphous form of berberine ursodeoxycholate in tetrahydrofuran/$H_2O$, wherein the tetrahydrofuran:$H_2O$ (v/v) is from about 1:2 to about 2:1; slowly evaporating tetrahydrofuran/$H_2O$; and collecting the precipitate by filtration to obtain Form I of berberine ursodeoxycholate.

In certain embodiments, the tetrahydrofuran:$H_2O$ (v/v) is about 1:1.

In yet another aspect, the invention generally relates to a method for preparing Form J of berberine ursodeoxycholate. The method includes: providing Form A of berberine ursodeoxycholate; heating Form A of berberine ursodeoxycholate to about 100° C. in $N_2$; and cooling the heated berberine ursodeoxycholate under $N_2$ to room temperature to obtain Form J of berberine ursodeoxycholate.

In certain embodiments, the Form A of berberine ursodeoxycholate is heated in $N_2$ for about 0.5 to about 2 hours.

In yet another aspect, the invention generally relates to a method for preparing Form P of berberine ursodeoxycholate. The method includes: providing Form A of berberine ursodeoxycholate; slurrying Form A of berberine ursodeoxycholate in MeOH/methyl ethyl ketone or MeOH/methy tert-butyl ether, wherein the MeOH:methyl ethyl ketone (v/v) is from about 1:8 to about 1:10 or MeOH:methyl tert-butyl ether (v/v) is from about 1:8 to about 1:10 at about 50° C.; and collecting the solid to obtain Form P of berberine ursodeoxycholate.

In certain embodiments, the slurrying is performed for about 6 to about 36 hours.

In certain embodiments, the MeOH:methyl tert-butyl ether (v/v) is 1:9.

In certain embodiments, the MeOH:methyl ethyl ketone (v/v) is 1:9.

In yet another aspect, the invention generally relates to a method for preparing Form W of berberine ursodeoxycholate. The method includes: providing Form A of berberine ursodeoxycholate; slurrying Form A of berberine ursodeoxycholate in cyclohexanone/n-butylacetate, wherein the cyclohexanone:n-butylacetate (v/v) is from about 1:3 to about 1:5 at room temperature; and collecting the solid to obtain Form W of berberine ursodeoxycholate.

In certain embodiments, the cyclohexanone:n-butylacetate (v/v) is about 1:4.

In certain embodiments, the slurrying is performed for about 6 to about 36 hours.

In yet another aspect, the invention generally relates to a method for preparing Form X of berberine ursodeoxycholate. The method includes: providing Form A of berberine ursodeoxycholate; dissolving Form A of berberine ursodeoxycholate in n-butanol; slowly evaporating n-butanol at room temperature; and collecting the precipitate by filtration to obtain Form X of berberine ursodeoxycholate.

In certain embodiments, evaporating n-butanol at room temperature is performed for about 6 to about 36 hours.

In a further aspect, the invention contemplates that any one of the solid forms of BBR-UDCA as disclosed herein can exist in the presence of the any other of the physical forms or mixtures thereof. Accordingly, in one embodiment, the invention provides the crystalline form or the amorphous form of BBR-UDCA or a pharmaceutical composition comprising the crystalline form or the amorphous form of BBR-UDCA as described herein, wherein the crystalline or amorphous form is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of BBR-UDCA. For example, in one embodiment is a solid form of BBR-UDCA comprising a crystalline form of BBR-UDCA that has any one of the powder X-ray diffraction patterns disclosed herein, wherein the solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of BBR-UDCA.

In certain embodiments, the invention relates to any of the above-referenced forms of BBR-UDCA, wherein the form is substantially pure (i.e., a substantially pure crystalline form or a substantially pure amorphous form).

A further aspect of the invention provides a pharmaceutical composition comprising the crystalline or amorphous forms of BBR-UDCA as disclosed herein. In a further aspect, the invention provides a pharmaceutical composition comprising a crystalline form or an amorphous form of BBR-UDCA as disclosed herein wherein the crystalline form or amorphous form is substantially pure. In a further aspect, the invention provides a method of preparing a pharmaceutical composition comprising combining a crystalline form or an amorphous form of BBR-UDCA as disclosed herein and a pharmaceutically acceptable excipient, carrier, or diluent. In a further aspect, the invention provides a method of preparing a pharmaceutical composition comprising combining a crystalline form or an amorphous form of BBR-UDCA as disclosed herein and a pharmaceutically acceptable excipient, carrier, or diluent, wherein the crystalline form or amorphous form is substantially pure. In a further aspect, the invention provides a pharmaceutical composition prepared by combining a crystalline form or an amorphous form of BBR-UDCA as disclosed herein and a pharmaceutically acceptable excipient, carrier, or diluent. In a further aspect, the invention provides a pharmaceutical composition prepared by combining a crystalline form or an amorphous form of BBR-UDCA as disclosed herein and a pharmaceutically acceptable excipient, carrier, or diluent wherein the crystalline form or amorphous form is substantially pure. In a further aspect, the invention provides an oral dosage form comprising the crystalline or amorphous forms of BBR-UDCA or pharmaceutical compositions disclosed herein. For example, in one embodiment, the oral dosage form is a tablet or capsule.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^3H$) and carbon-14 ($^{14}C$) labeled compounds are particularly preferred for their ease of preparation and detectability. Further, substitution with heavier isotopes such as deuterium ($^2H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^1H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

Solvates and polymorphs of the compounds of the invention are also contemplated herein. Solvates of the compounds of the present invention include, for example, hydrates.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the disease or condition being treated or the nature of the therapy being used and on the nature of the active compound.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

The following examples are meant to be illustrative of the practice of the invention, and not limiting in any way.

EXAMPLES

The examples below, including preparation and analysis, further illustrate and exemplify particular aspects and embodiments of the invention. It is to be understood that the scope of the present invention is not limited by the scope of the following examples.

General Method 1. X-Ray Powder Diffraction (XRPD)

The XRPD data were collected according to the following general protocol.

Instrument Method

XRPD patterns were collected on a PANalytical X-ray powder diffractometer fitted with an automatic sample changer, a theta-theta goniometer, automatic beam divergence slit and a PSD Vantec-1 detector. The X-ray tube voltage and amperage were set to 45 kV and 40 mA respectively. The diffractometer was aligned and a calibration check performed using a corundum reference material on the day of data collection. XRPD parameters used are listed in Table 1. Data were collected and analyzed by the software Data Viewer.

TABLE 1

Parameters for XRPD Tests

| Parameters | Model | |
|---|---|---|
| | Empyrean | X' Pert³ |
| Mode | Reflection | Reflection |
| X-Ray wavelength | Cu, kα | |
| | Kα1 (Å): 1.540598, | |
| | Kα2 (Å): 1.544426, | |
| | Kα2/Kα1 intensity ratio: 0.50 | |
| X-Ray tube setting | 45 kV, 40 mA | |
| Divergence slit | Automatic | Fixed 1/8° |
| Scan mode | Continuous | |
| Scan range (°2Theta) | 3-40 | |
| Scan step time (s) | 17.8 | 46.7 |
| Step size (°2Theta) | 0.0167 | 0.0263 |
| Test Time | ~5 min 30 s | ~5 min 4 s |

General Method 2. Single-Crystal X-Ray Diffraction (SCXRD)

The SCXRD data were collected at 153 K using BRUKER D8 VENTURE diffractometer (Mo/Kα radiation, λ=0.710 Å). The polarized light microscopic picture was captured using Shanghai Cewei PXS9-T stereomicroscope.

General Method 3. Differential Scanning Calorimetry (DSC)

DSC was performed using a TA Q200/Q2000 from TA Instruments. Detailed parameters used are listed in Table 2.

TABLE 2

Parameters for DSC Tests

| Parameters | DSC |
| --- | --- |
| Method | Ramp |
| Sample pan | Aluminum, sealed/open |
| Temperature | 25° C.-Setting temperature |
| Heating rate | 10° C./min |
| Purge gas | $N_2$ |

General Method 4. Thermo Gravimetric Analysis (TGA)

The TGA data were collected using a TA Q500/Q5000 TGA from TA Instruments. Detailed parameters used are listed in Table 3.

TABLE 3

Parameters for TGA Tests

| Parameters | TGA |
| --- | --- |
| Method | Ramp |
| Sample pan | Aluminum, open |
| Temperature | Room temperature-Setting temperature |
| Heating rate | 10° C./min |
| Purge gas | $N_2$ |

General Method 5. Dynamic Vapor Sorption (DVS)

DVS was measured via a SMS (Surface Measurement Systems) DVS Intrinsic. Parameters for DVS test are listed in Table 4.

TABLE 4

Parameters for DVS Tests

| Parameters | Values |
| --- | --- |
| Temperature | 25° C. |
| Sample size | 10-20 mg |
| Gas and flow rate | $N_2$, 200 mL/min |
| dm/dt | 0.002%/min |
| Min.dm/dt stability duration | 10 min |
| Max. equilibrium time | 360 min |
| RH range | 0% RH-95% RH-0% RH for anhydrous forms |
| | 60% RH-95% RH-0% RH-95% RH for hydrous forms |
| RH step size | 10% for 90% RH-0% RH and 0% RH-90% RH |
| | 5% for 95% RH-90% RH and 90% RH-95% RH |

General Method 6. Solution Nuclear Magnetic Resonance (NMR)

Solution NMR was collected on Bruker 400M NMR Spectrometer using DMSO-$d_6$.

General Method 7. High Performance Liquid Chromatography (HPLC)

Agilent 1260/1100 HPLC was utilized and detailed chromatographic conditions for purity and solubility measurement are listed in Table 5.

TABLE 5

HPLC-DAD Methods for Purity and Solubility Tests

| Parameters | Agilent 1260/1100 DAD Detector | | | |
| --- | --- | --- | --- | --- |
| Column | Cosmosil C18 5 um 150 × 4.6 mm | | | |
| Mobile phase | A: 10 mM $NaH_2PO_4$ in $H_2O$ (pH 2.2) | | | |
| | B: Acetonitrile | | | |
| | Purity | | Solubility | |
| | Time (min) | % B | Time (min) | % B |
| Gradient table | 0.0 | 20 | 0.0 | 20 |
| | 15.0 | 45 | 6.0 | 60 |
| | 25.0 | 90 | 7.0 | 60 |
| | 30.0 | 90 | 7.1 | 20 |
| | 30.1 | 20 | 10.0 | 20 |
| | 35.0 | 20 | — | — |
| Run time | 35.0 min | | 10.0 min | |
| Post time | 0.0 min | | | |
| Flow rate | 1.0 mL/min | | | |
| Injection volume | 5 μL | | | |
| Detector wavelength | UV at 220 nm, reference 500 nm | | | |
| Column temperature | 30° C. | | | |
| Sampler temperature | RT | | | |
| Diluent | Acetonitrile:$H_2O$ (1:1, v/v) | | | |

TABLE 6

HPLC-ELSD Methods for Solubility Tests

| Parameters | Agilent 1100 ELSD Detector | |
| --- | --- | --- |
| Column | Waters symmetry shield RP18 3.5 um 150 × 4.6 mm | |
| Mobile phase | A: 0.1% TFA in $H_2O$ | |
| | B: 0.1% TFA in acetonitrile | |
| | Time (min) | % B |
| Gradient table | 0.0 | 25 |
| | 10.0 | 90 |
| | 11.0 | 90 |
| | 11.1 | 25 |
| | 15.0 | 25 |
| Run time | 15.0 min | |
| Flow rate | 1.0 mL/min | |
| Injection volume | 5 μL | |
| Detector | ELSD | |
| Column temperature | 40° C. | |
| Sampler temperature | RT | |
| Diluent | Acetonitrile:$H_2O$ (1:1, v/v) | |
| ELSD | Alltech 3300 | |
| Temperature | 50° C. | |
| Gain | 2 | |
| gas flow | 3.0 L/min | |

Form A of Berberine Ursodeoxycholate

Preparation and Characterization of Form A 5 g BBR-UDCA (mixed crystal or amorphous form) was added into 20 mL EtOH/$H_2O$ (1:10, v/v). The mixture was stirred at room temperature for 5 hours, and then the mixture was filtered. The filter cake was washed with distilled water. Form A (4.3 g) was obtained.

XRPD and TGA Analysis of Form A

Figure 12:
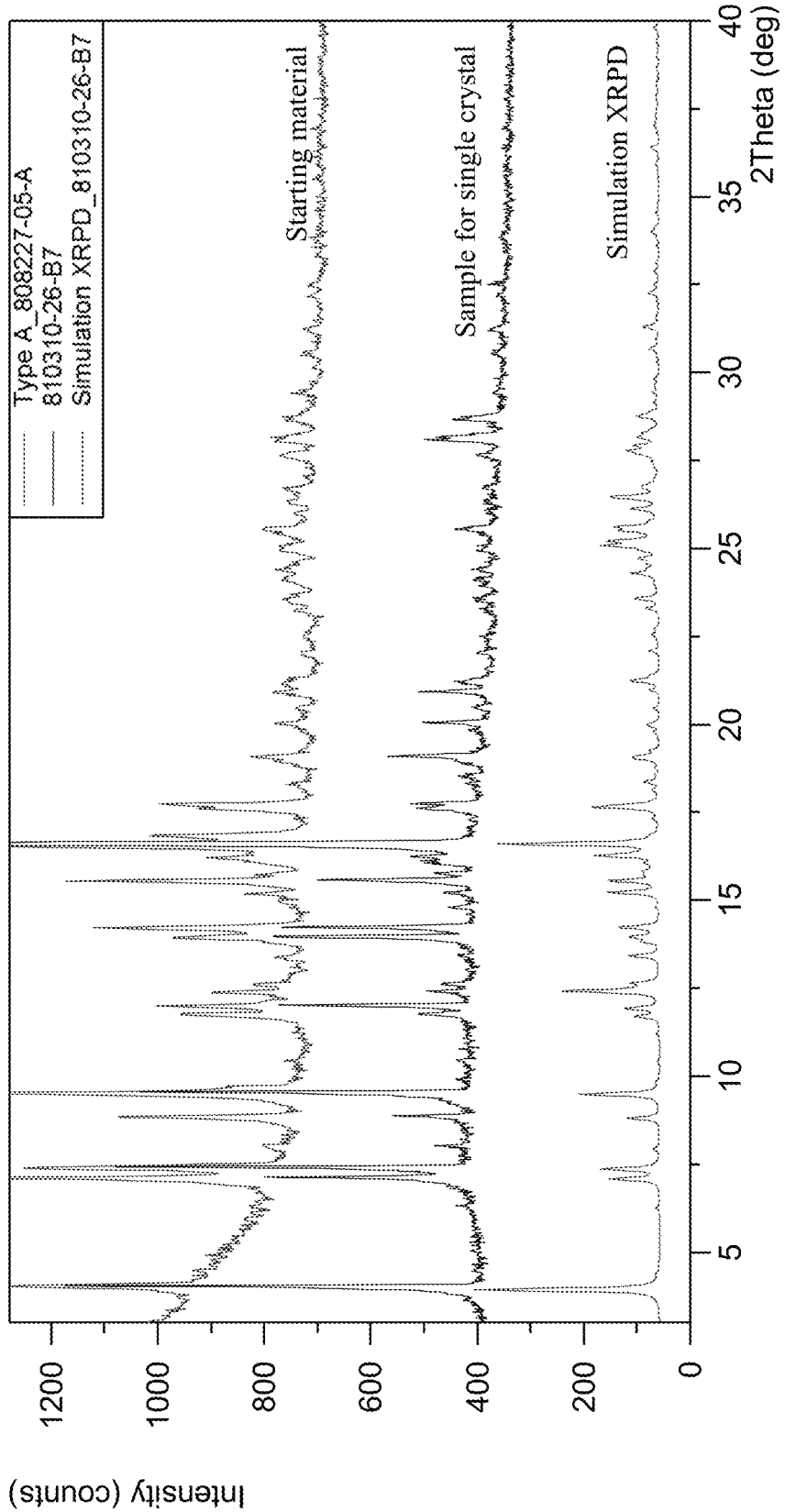
FIG. 12 shows an overlay of XRPD patterns of Form A of BBR-UDCA and hemi-nonahydrate single crystal of BBR-UDCA.
Figure 28:
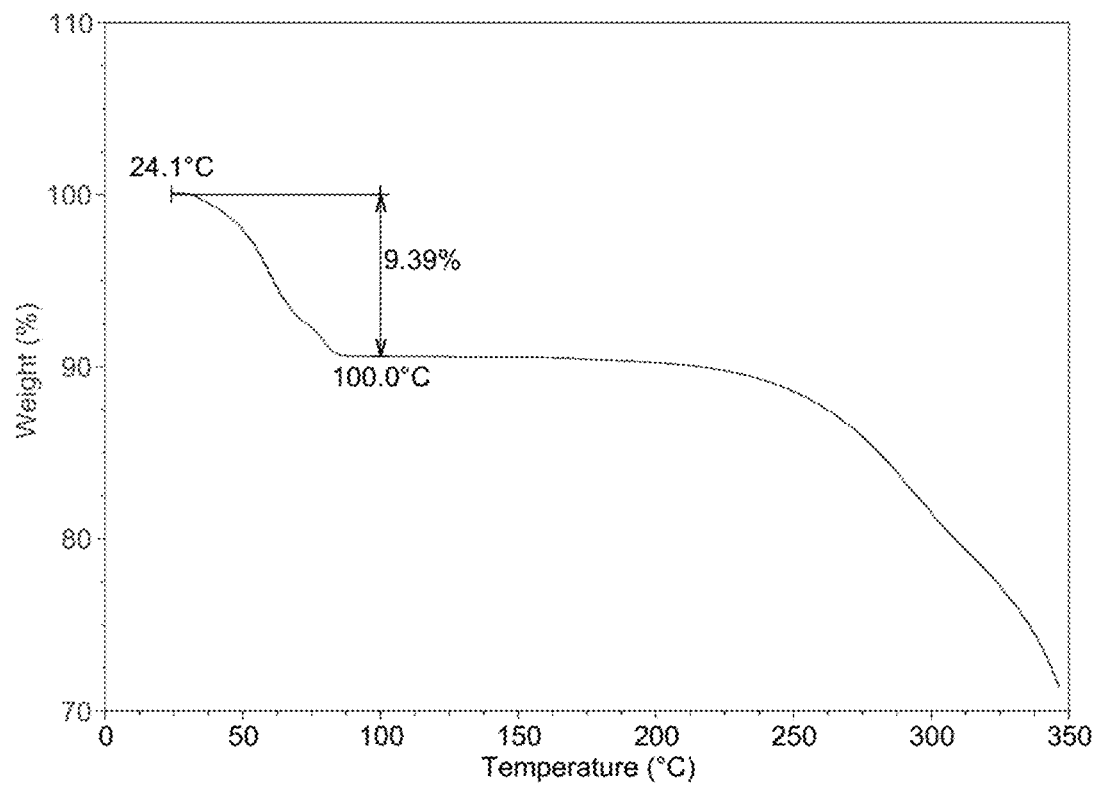
FIG. 28 shows an embodiment of a TGA graph of Form A of BBR-UDCA.
Figure 29:
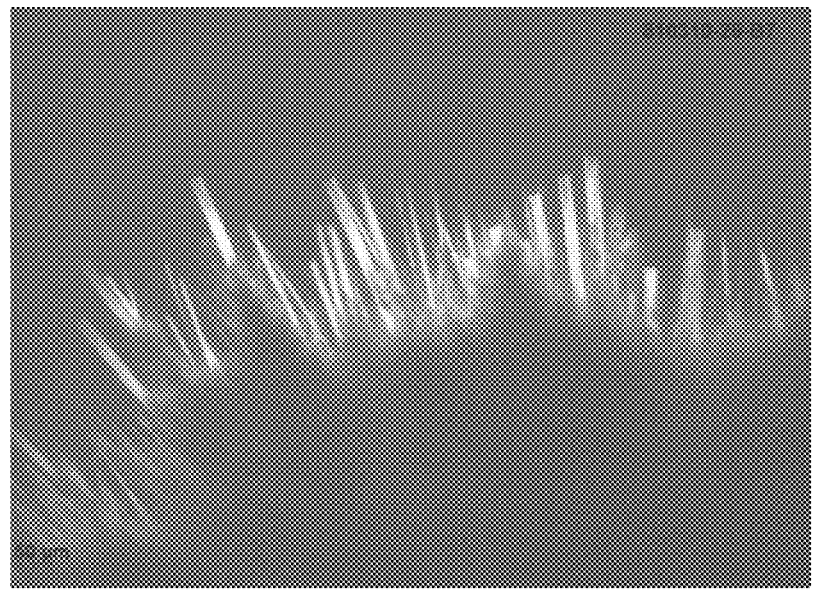
FIG. 29 shows an embodiment of microscopic photo of single crystalline Form A of BBR-UDCA.
Figure 30:
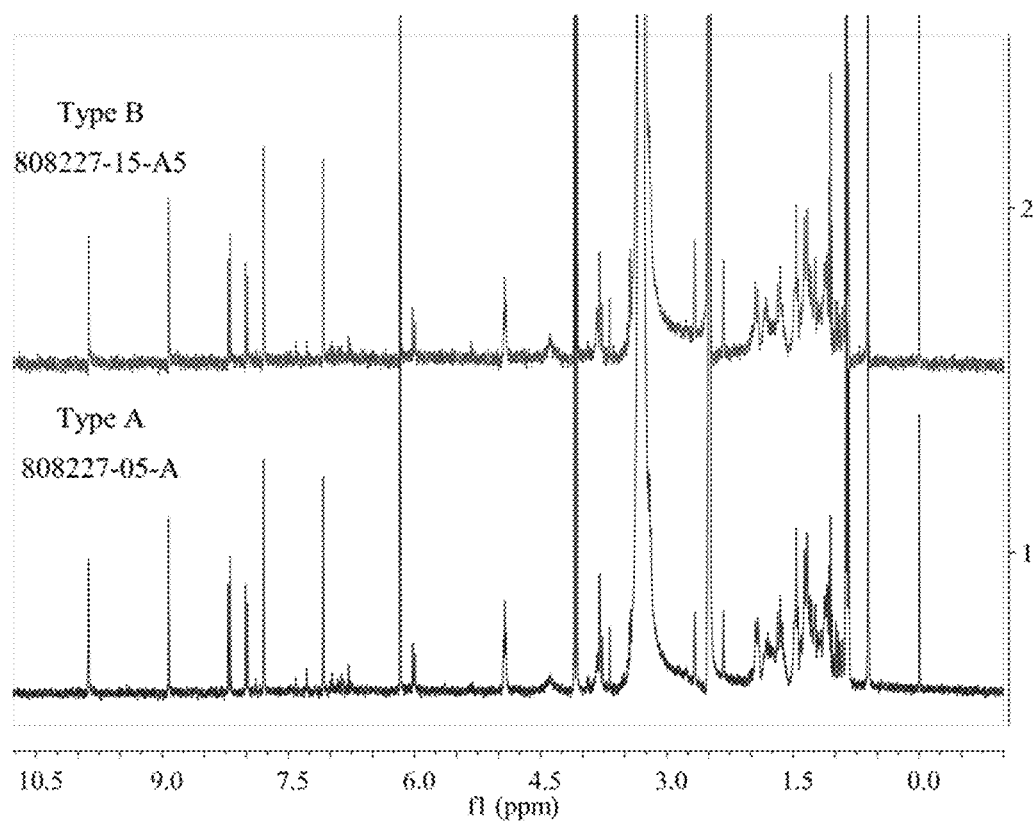
FIG. 30 shows an embodiment of $^1$H NMR spectra of Form A of BBR-UDCA (bottom) and Form B of BBR-UDCA (top).
Figure 31:
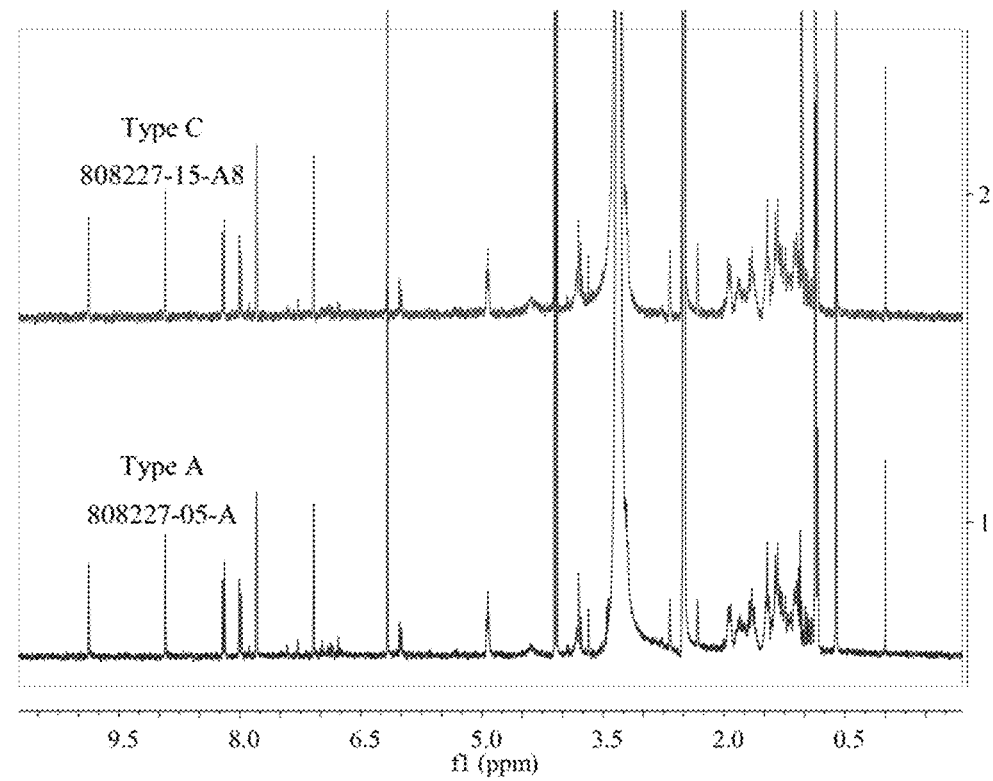
FIG. 31 shows an embodiment of $^1$H NMR spectra of Form A of BBR-UDCA (bottom) and Form C of BBR-UDCA (top).
Figure 32:
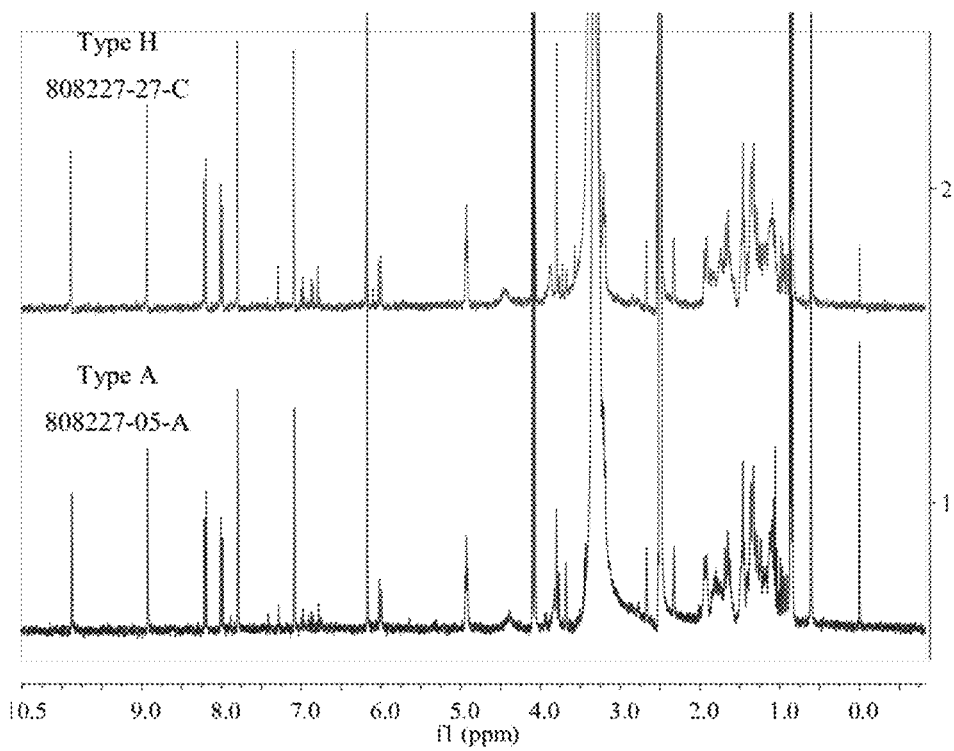
FIG. 32 shows an embodiment of $^1$H NMR spectra of Form A of BBR-UDCA (bottom) and Form H of BBR-UDCA (top).
Figure 33:
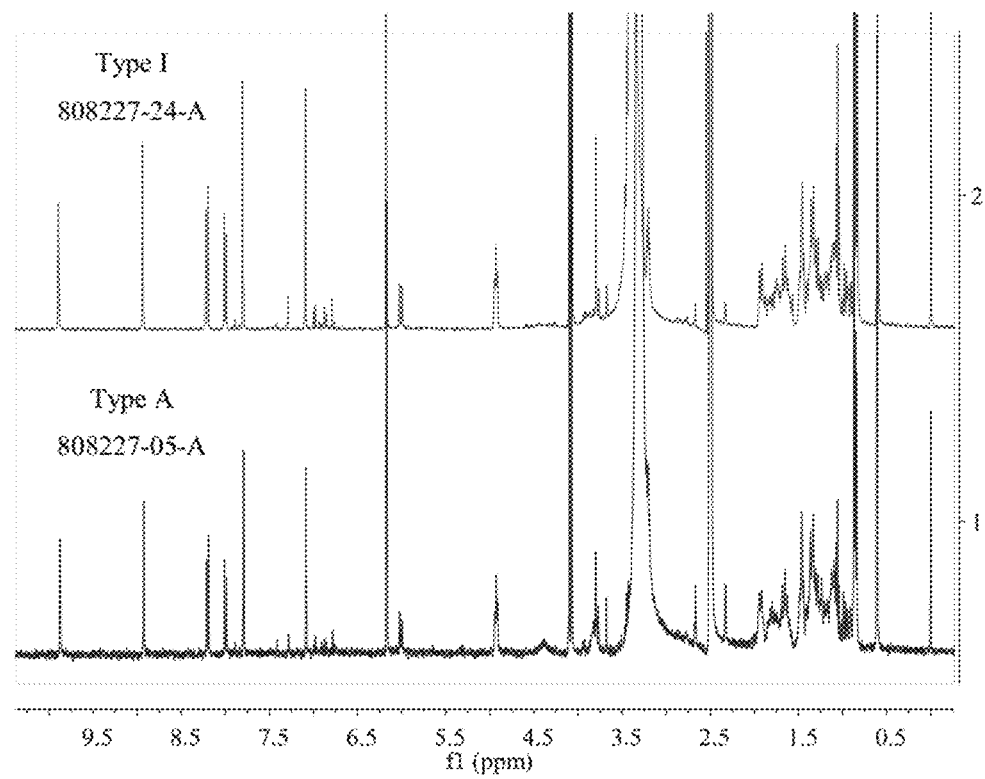
FIG. 33 shows an embodiment of $^1$H NMR spectra of Form A of BBR-UDCA (bottom) and Form I of BBR-UDCA (top).
Figure 34:
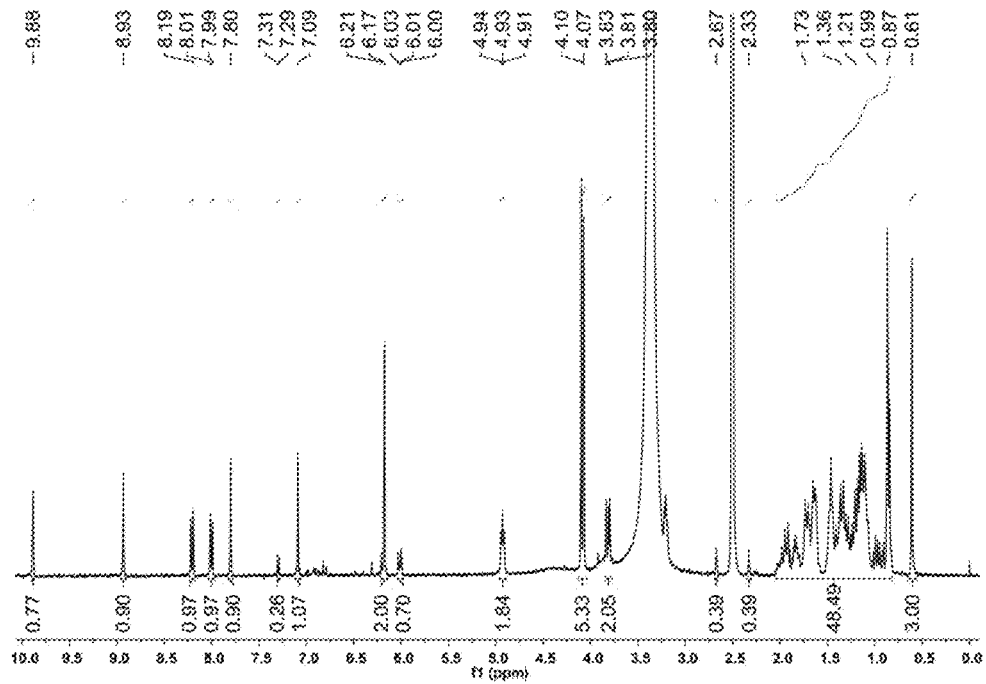
FIG. 34 shows an embodiment of $^1$H NMR spectra of Form W of BBR-UDCA.
Figure 35:
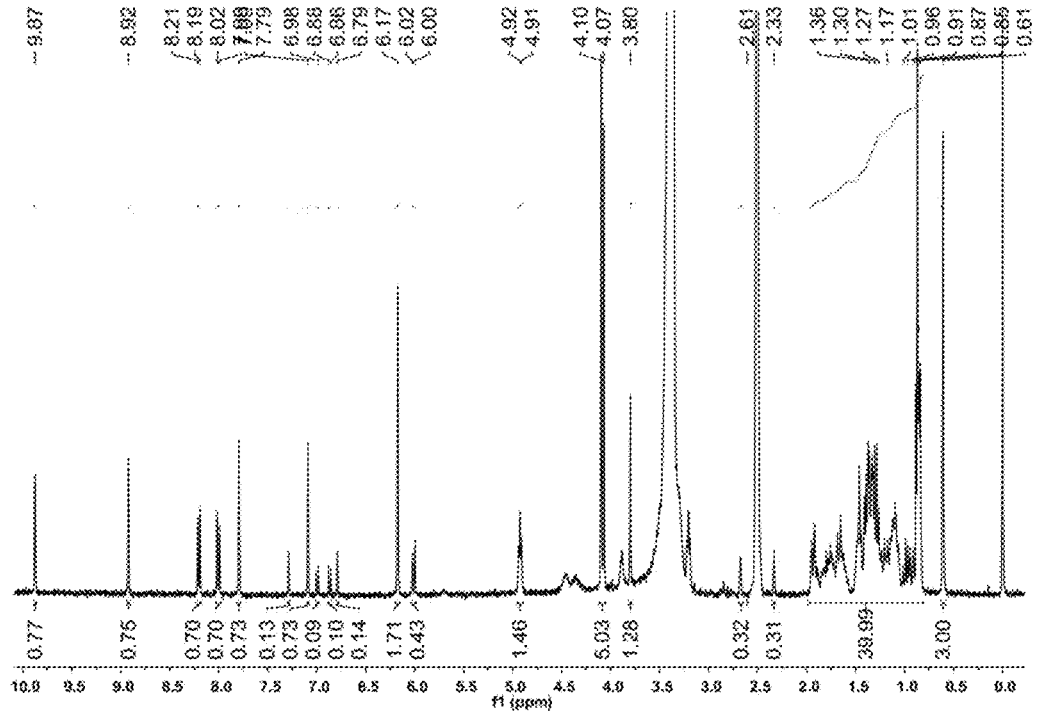
FIG. 35 shows an embodiment of $^1$H NMR spectra of Form X of BBR-UDCA.

The XRPD (FIG. 1) pattern comprised peaks at 2θ values of 3.98, 7.06, 7.34, 7.93, 8.79, 9.47, 11.70, 11.94, 12.34, 12.55, 13.90, 14.17, 15.14, 15.50, 16.16, 16.54, 16.78, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49°. The XRPD overlay (FIG. 12) showed the experimental XRPD pattern of this sample matched well with the calculate pattern derived from the single crystal structure, indicating the sample was a hemi-nonahydrate. The TGA data was shown in FIG. 28. A weight loss of 9.4% was observed (theoretical weight loss of hemi-nonahydrate was 10.0%) up to 100° C.

Form B of Berberine Ursodeoxycholate
Preparation and Characterization of Form B 5 g BBR-UDCA was dissolved in ACN/H$_2$O (1:1, v/v) solution. Type B (1.6 g) was obtained via slow evaporation from ACN/H$_2$O (1:1, v/v) solution.

XRPD, DSC and TGA Analysis of Form B

The XRPD (FIG. 2) pattern comprised peaks at 2θ values of 7.39, 9.31, 12.41, 13.14, 14.37, 14.76, 15.53, 18.65, 21.79, 22.87, 25.27, 25.53 and 28.12°. TGA/DSC data was shown in FIG. 20. A weight loss of 12.2% was found when heated up to 150° C. Two endotherms at 78.1° C. and 91.2° C. (onset temperatures) were observed.

Form C of Berberine Ursodeoxycholate
Preparation of Form C

Type C of BBR-UDCA (1.8 g) was obtained via slow evaporation from isopropyl alcohol/isopropyl acetate (IPA/IPAc) (1:1, v/v) solution of 5 g BBR-UDCA.

XRPD, DSC and TGA analysis of Form C

The XRPD (FIG. 3) pattern comprised peaks at 2θ values of 7.23, 10.42, 12.10, 13.37, 14.24, 14.48, 15.28, 15.95, 17.00, 18.17, 20.12, 21.77 and 25.47°. TGA/DSC data (FIG. 21) showed a weight loss of 11.6% when being heated up to 150° C. with two endotherms at 68.4° C. and 183.3° C. (onset temperatures).

Form D of Berberine Ursodeoxycholate
Preparation of Form D 5 g Form A of BBR-UDCA was added into ethyl acetate (aw≤0.2). The obtained suspension was stirred at room temperature for 5 hours, and then the mixture was filtered. Form D of BBR-UDCA (4.3 g) was obtained.

XRPD, DSC and TGA analysis of Form D

The XRPD (FIG. 4) pattern comprised peaks at 2θ values of 4.24, 6.79, 8.50, 10.25, 11.50, 13.62, 14.74, 15.20, 17.92, 18.39, 22.91 and 25.73°. TGA/DSC data (FIG. 22) showed a weight loss of 2.2% after heating to 150° C. and an endotherm at 185.2° C. (onset temperature).

Form E of Berberine Ursodeoxycholate
Preparation of Form E 5 g Form A of BBR-UDCA was added into dichloromethane (DCM) atmosphere. Type E (4.5 g) was obtained via solid vapor diffusion in DCM after 24 hours.

XRPD, DSC and TGA analysis of Form E

The XRPD (FIG. 5) pattern comprised peaks at 2θ values of 8.59, 10.55, 11.36, 11.86, 12.46, 13.08, 13.38, 14.34, 15.57, 17.24, 17.72, 18.43, 19.66, 19.84, 20.35, 20.91, 21.36, 21.95, 23.21, 24.67, 25.04, 25.82, 26.12, 27.01, 27.84, 28.97, 30.35, 33.33, 34.54 and 36.06°.

Form H of Berberine Ursodeoxycholate
Preparation of Form H 5 g BBR-UDCA was dissolved into acetonitrile/H$_2$O (1:1, v/v). After slow evaporation of the solvents, the precipitate was collected by filtration. The obtained solid was heated to 100° C. for 0.5-2 hours, and then it was cooled to room temperature. Form H of BBR-UDCA (0.8 g) was obtained.

XRPD, DSC and TGA analysis of Form H

The XRPD (FIG. 6) pattern comprised peaks at 2θ values of 13.05, 14.63 and 25.46°. TGA/DSC data (FIG. 23) showed a weight loss of 7.9% after heating to 150° C., with an endotherm at 97.1° C. (peak temperature) and an endotherm at 138.3° C. (onset temperature).

Form I of Berberine Ursodeoxycholate
Preparation of Form I 5 g BBR-UDCA was dissolved into tetrahydrofuran/H$_2$O (1:1, v/v). After slow evaporation of the solvents for 24 hours, the precipitate was collected by filtration. Form I of BBR-UDCA (0.9 g) was obtained.

XRPD, DSC and TGA analysis of Form I

The XRPD (FIG. 7) pattern comprised peaks at 2θ values of 4.19, 7.64, 10.03, 13.32, 13.84, 14.83, 16.73, 22.73, 25.61 and 28.57°. TGA/DSC data (FIG. 24) showed a weight loss of 10.7% after heating to 150° C., with an endotherm at 56.2° C. (onset temperature) and an endotherm at 79.6° C. (onset temperature).

Form J of Berberine Ursodeoxycholate
Preparation of Form J 5 g Form A of BBR-UDCA was heated to 100° C. in N$_2$ for 0.5-2 hours, and then it was cooled to room temperature with N$_2$ protection. Form J of BBR-UDCA (4.4 g) was obtained.

XRPD, DSC and TGA analysis of Form J

The XRPD (FIG. 8) pattern comprised peaks at 2θ values of 4.61, 6.32, 7.38, 8.22, 9.21, 10.57, 11.73, 12.13, 12.62, 12.96, 13.87, 14.55, 14.78, 15.81, 16.48, 17.69, 18.39, 19.01, 20.06, 21.25, 22.13, 23.20, 24.47, 24.89, 26.31, 27.98, 30.25 and 33.35°.

Form J converts to Form A with air exposure.

Form P of Berberine Ursodeoxycholate
Preparation of Form P

Form P of BBR-UDCA (3.8 g) was obtained via slurrying 5 g Form A of BBR-UDCA in MeOH/methyl ethyl ketone (1:9, v/v) at 50° C. for one day.

XRPD, DSC and TGA analysis of Form P

The XRPD (FIG. 9) pattern comprised peaks at 2θ values of 3.11, 5.01, 5.78, 7.26, 9.20, 10.10, 10.79, 11.65, 13.70, 14.59, 15.22, 16.19, 16.54, 17.05, 18.06, 18.68, 20.52, 21.09, 21.73, 22.49, 24.73, 25.42, 25.94 and 30.11°. TGA/DSC data (FIG. 25) showed a weight loss of 8.8% after heating to 150° C., with an endotherm at 100.3° C. (peak temperature), an endotherm at 122.5° C. (peak temperature), and 168.7° C. (peak temperature).

Form W of Berberine Ursodeoxycholate
Preparation of Form W

Form W of BBR-UDCA (4.0 g) was obtained via slurrying 5.0 g Form A of BBR-UDCA in cyclohexanone/n-butylacetate (1:4, v/v) at room temperature for one day.

XRPD, DSC and TGA analysis of Form W

The XRPD (FIG. 10) pattern comprised peaks at 2θ values of 6.49, 7.16, 8.51, 10.21, 12.01, 13.13, 13.90, 14.42, 15.18, 15.57, 16.03, 16.45, 16.74, 17.08, 17.85, 18.39, 19.61, 20.43, 21.39, 21.70, 23.51 and 25.21°. TGA/DSC data (FIG. 26) showed a weight loss of 7.2% after heating to 110° C., with an endotherm at 82.1° C. (peak temperature) and an endotherm at 106.4° C. (peak temperature).

Form X of Berberine Ursodeoxycholate
Preparation of Form X 5 g Form A of BBR-UDCA was dissolved in n-butanol. After slow evaporation of the solvent at room temperature for 24 hours, the precipitate was collected by filtration. Form X of BBR-UDCA (0.8 g) was obtained.

XRPD, DSC and TGA analysis of Form X

The XRPD (FIG. 11) pattern comprised peaks at 2θ values of 3.63, 6.61, 7.24, 10.49, 11.95, 13.51, 14.26, 14.54, 15.14, 16.01, 16.82, 18.28, 20.26, 21.08, 21.49, 21.90, 25.60, 26.40, 27.31, 29.34, 30.59, 31.01, 34.04, 34.68 and 36.91°. TGA/DSC data (FIG. 27) showed a weight loss of 17.0% after heating to 140° C., and an endotherm at 86.7° C. (peak temperature) and an endotherm at 189.1° C. (peak temperature) were observed.

Stability Evaluation

Figure 13:
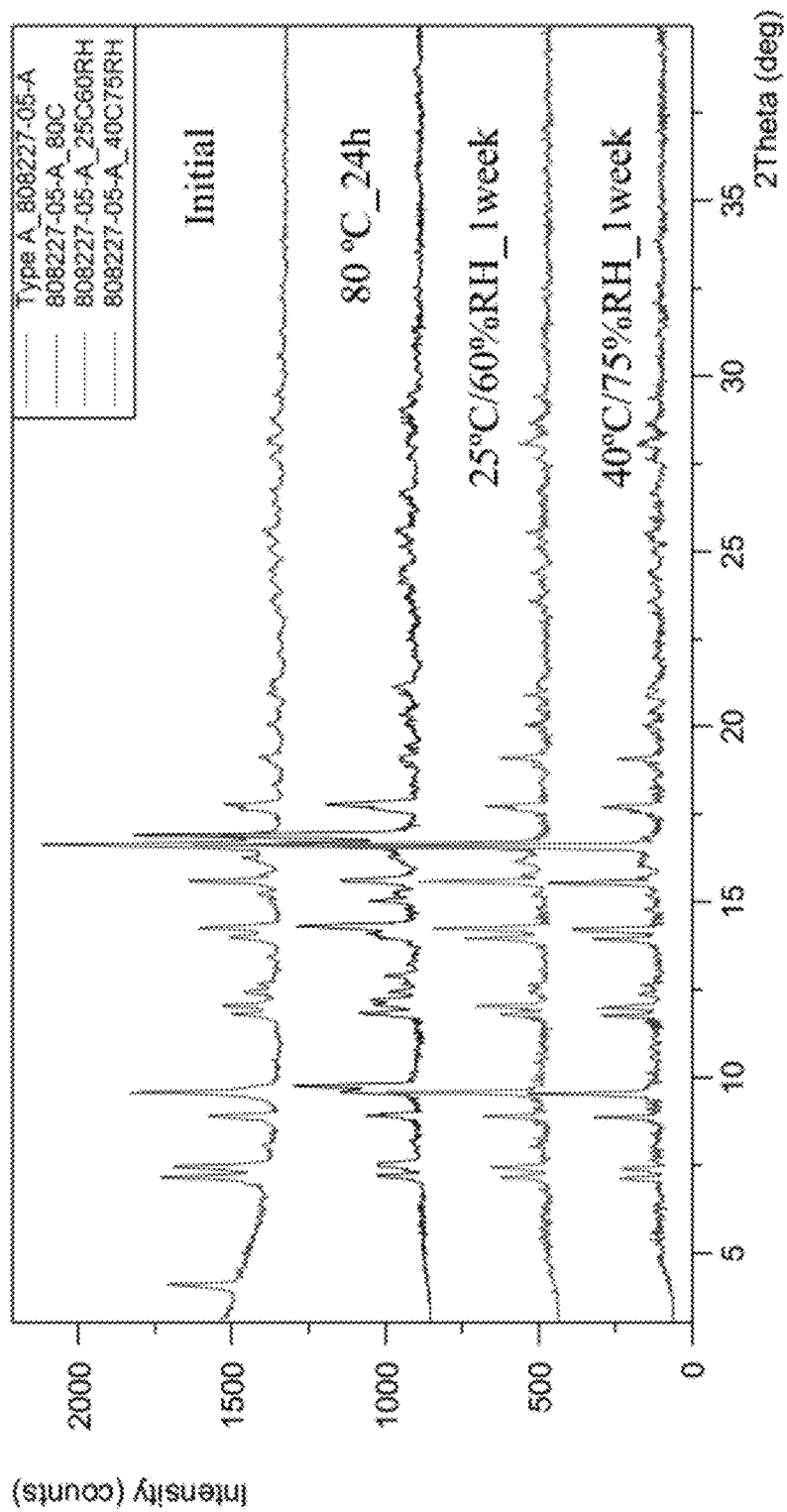
FIG. 13 shows an overlay of XRPD patterns of Form A of BBR-UDCA after stability evaluation.
Figure 14:
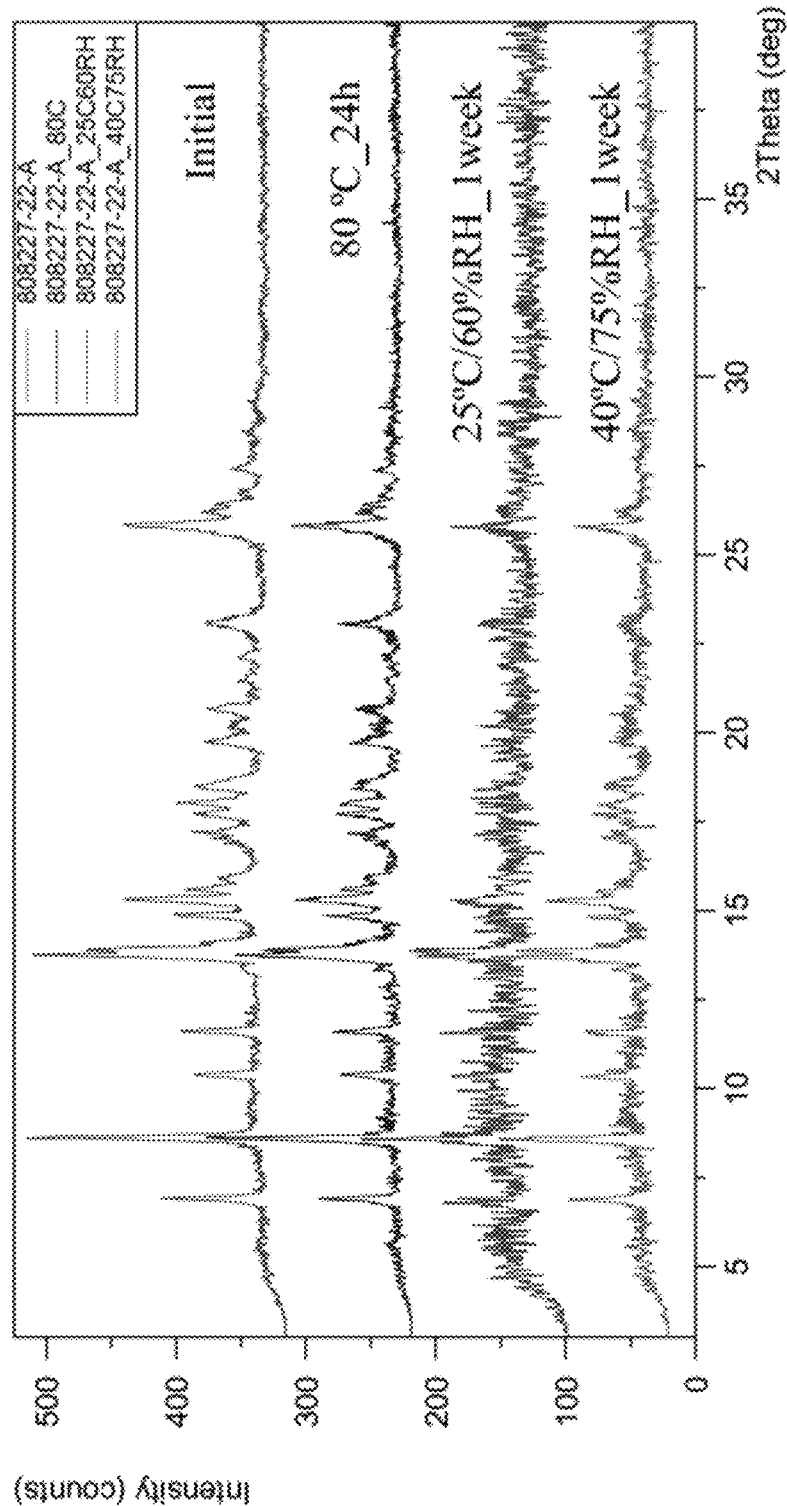
FIG. 14 shows an overlay of XRPD patterns of Form D of BBR-UDCA after stability evaluation.

To evaluate the physical and chemical stability of Form A of BBR-UDCA and Form D of BBR-UDCA, samples were stored at 80° C. (sealed) for 24 hours, 25° C./60% RH (open) and 40° C./75% RH (open) for one week. Both the samples were characterized using XRPD and HPLC, with the results summarized in the following table. XRPD results in FIG. 13 and FIG. 14 showed no crystal-form change for both Form A and D under all three conditions. The physical stability of Form A was better than Form D based on the 1-week stability results at 25° C./60% RH (open) and 40° C./75% RH (open).

With the HPLC-DAD result, no HPLC purity decrease was observed for Form A and a decrease of purity (0.5-1.7 area %) was observed for Form D under all three conditions, which indicated the slight degradation of Form D.

TABLE 7

Accelerated Stability Evaluation Summary of Form A and D

| Starting Material | Time point | Condition | Form | Purity (Area %) | Purity/ Initial purity (%) |
|---|---|---|---|---|---|
| Form A | Initial | — | Form A | 99.5 | — |
| | 24 hours | 80° C. | Form A | 99.3 | 99.8 |
| | 1 week | 25° C./60% RH | Form A | 99.4 | 99.9 |
| | 1 week | 40° C./75% RH | Form A | 99.4 | 99.8 |
| Form D | Initial | — | Form D | 99.6 | — |
| | 24 hours | 80° C. | Form D | 99.0 | 99.5 |
| | 1 week | 25° C./60% RH | Form D* | 98.9 | 99.3 |
| | 1 week | 40° C./75% RH | Form D* | 97.9 | 98.3 |

*According to FIG. 14, degree of crystallinity decreased.

Samples of Form A of BBR-UDCA, Form D of BBR-UDCA and BBR-UDCA (mixed crystals without quality control on crystal forms) were stored 25° C./60% RH (sealed) and 40° C./75% RH (sealed) for one month. All the samples were characterized using XRPD and HPLC, with the results summarized in the following table. No crystal-form change for both Form A and D under all three conditions. Both Form A and Form D showed better chemical stability compared to the mixed crystals of BBR-UDCA

TABLE 8

1-Month Stability Evaluation Summary

| Starting Material | Time Point | Condition | Crystal Form | Purity (Area %) | Purity/ Initial Purity(%) |
|---|---|---|---|---|---|
| Form A | Initial | — | Form A | 99.5 | — |
| | 1 Month | 25° C./60% RH | Form A | 99.3 | 99.8 |
| | 1 Month | 40° C./75% RH | Form A | 99.4 | 99.9 |
| Form D | Initial | — | Form D | 99.6 | — |
| | 1 Month | 25° C./60% RH | Form D | 97.2 | 97.6 |
| | 1 Month | 40° C./75% RH | Form D | 94.7 | 95.1 |
| Mixed crystal | Initial | — | Mixed | 99.0 | — |
| | 1 Month | 25° C./60% RH | Mixed | 90.8 | 91.7 |
| | 1 Month | 40° C./75% RH | Mixed | 88.7 | 89.6 |

Hygroscopicity Evaluation

Figure 15:
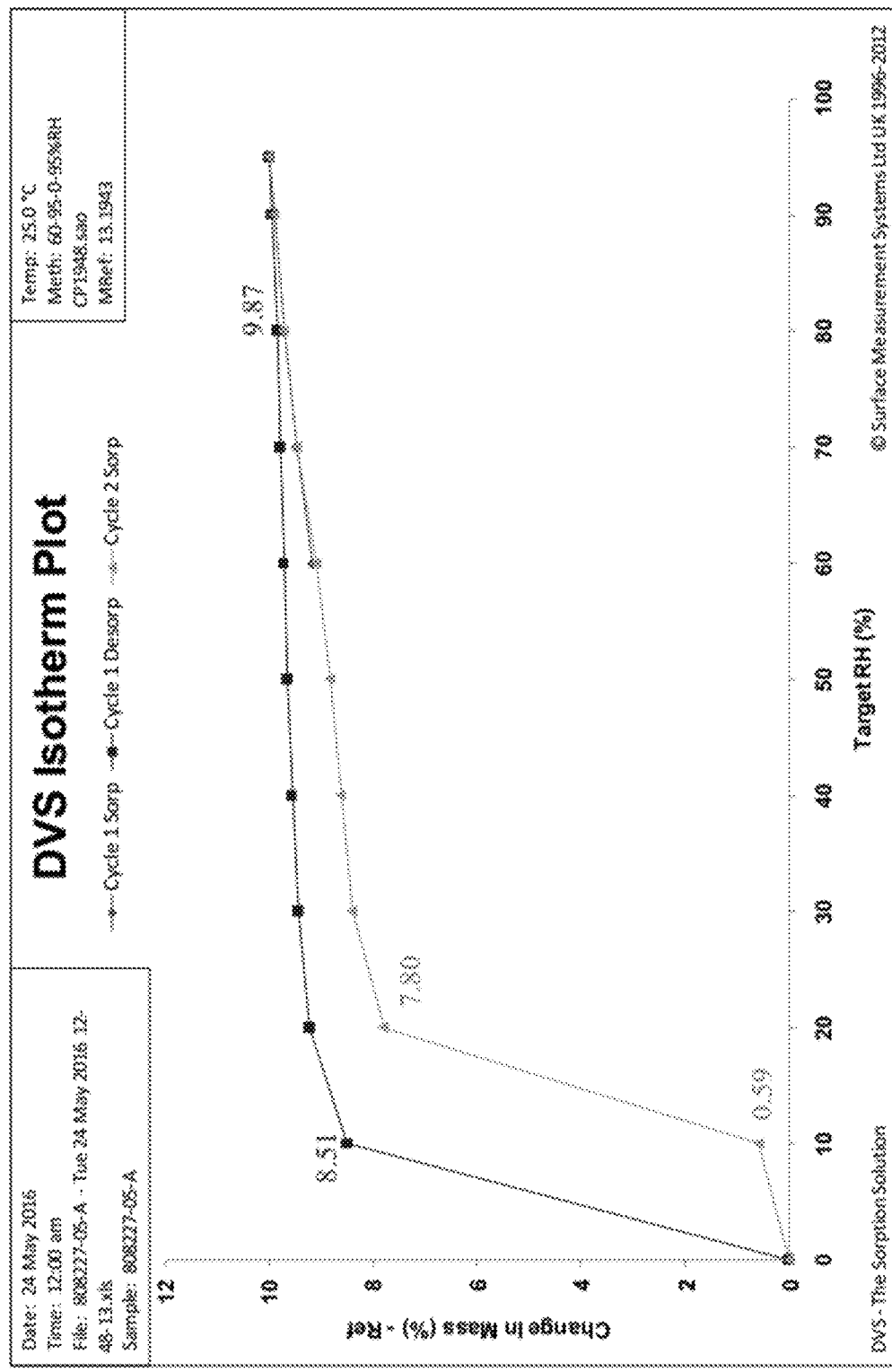
FIG. 15 shows an embodiment of a DVS graph of Form A of BBR-UDCA.
Figure 16:
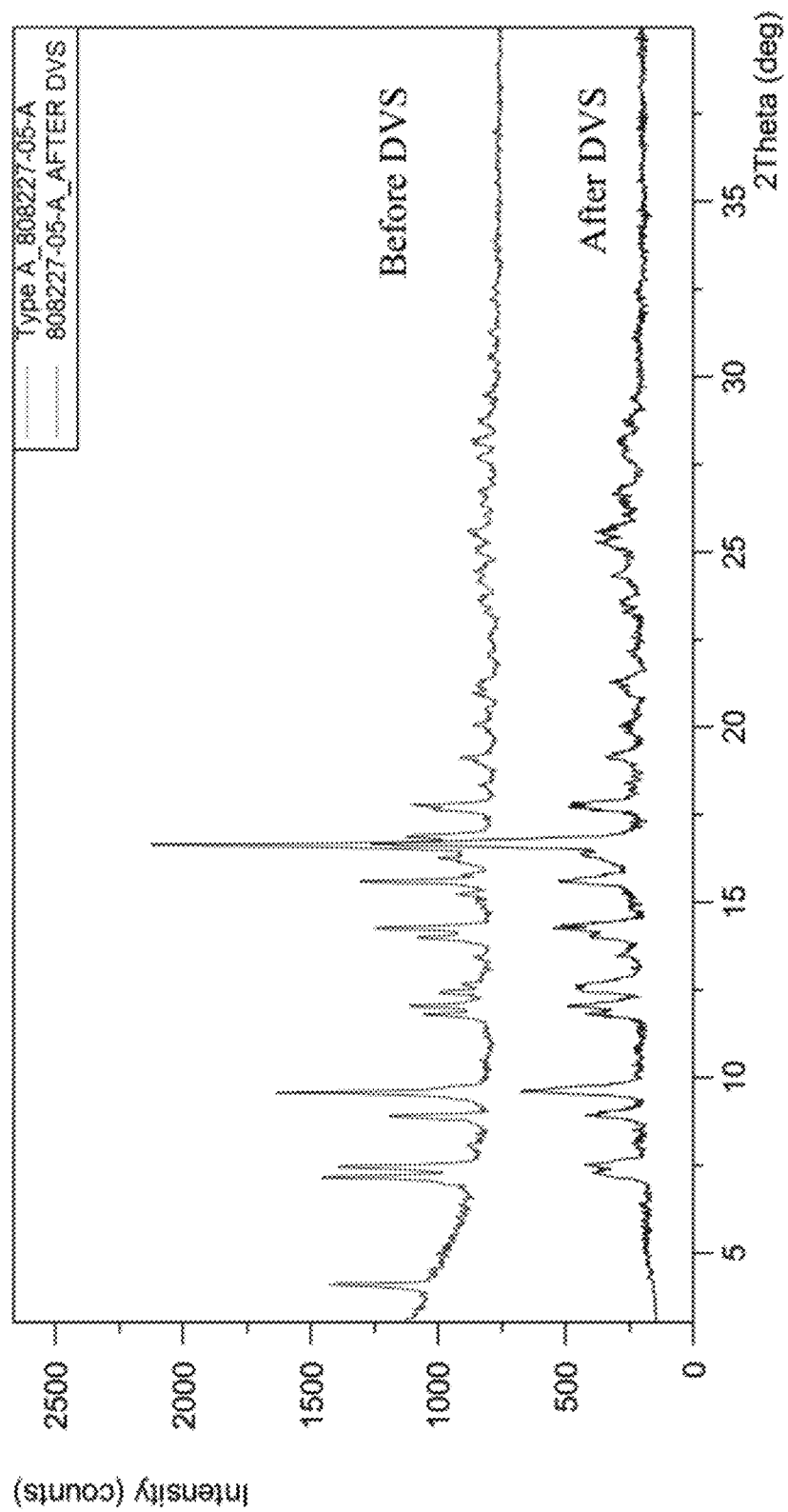
FIG. 16 shows an embodiment of an overlay of XRPD patterns of Form A of BBR-UDCA before and after DVS testing.

Dynamic Vapor Sorption (DVS) isotherm plot of Form A of BBR-UDCA was collected at 25° C. with the various humidity, 60% RH-95% RH-0% RH-95% RH (60% RH was the ambient humidity). The result is shown in FIG. 15. As the DVS plot shown, a step-like weight loss was observed between 10% RH and 20% RH. A water uptake of 9.9% was observed at 25° C./80% RH, which matched to the TGA weight loss. The XRPD overlay shown in FIG. 16 indicated that there was no crystal-form change after DVS, which indicated the good physical stability of Form A.

Figure 17:
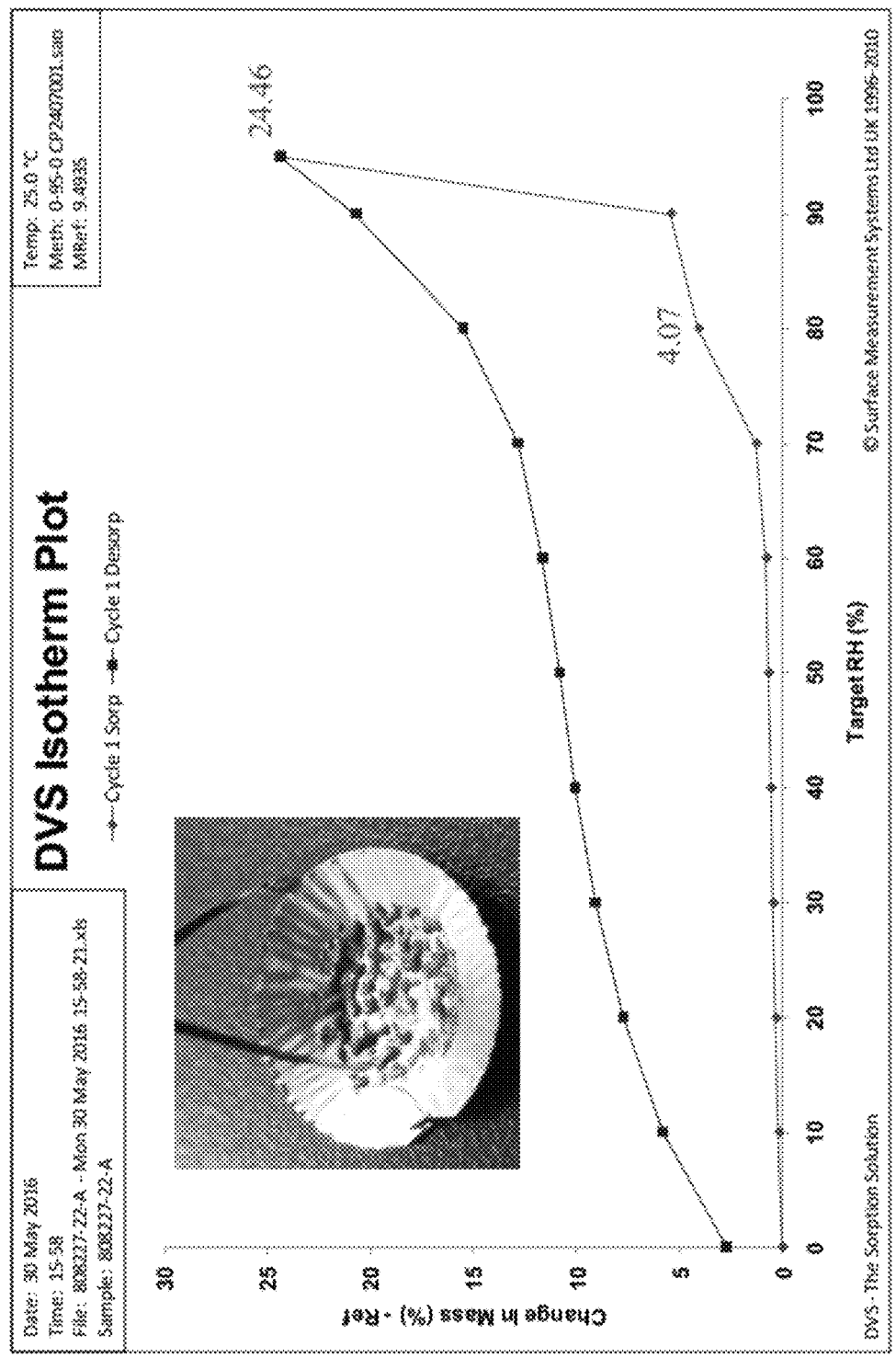
FIG. 17 shows an embodiment of a DVS graph of Form D of BBR-UDCA.

To investigate the hygroscopicity of Form D of BBR-UDCA, DVS isotherm plot of Form D was collected at 25° C. between 0 and 95% RH. The result is shown in FIG. 17. A water uptake of 4.1% was observed at 25° C./80% RH, while obvious increase was observed over 90% RH and 24.5% water uptake at 95% RH. The result of DVS test indicated Form D was deliquesced in high humidity.

Polarized Light Microscopy (PLM)

PLM characterizations of Form A of BBR-UDCA and Form D of BBR-UDCA were performed for observation of the morphology of the samples. Needle-like particles were observed in Form A sample and the particle size was 20 μm to 50 μm. For Type D sample, the particle size was approximately 10 μm.

Equilibrium Aqueous Solubility

Figure 18:
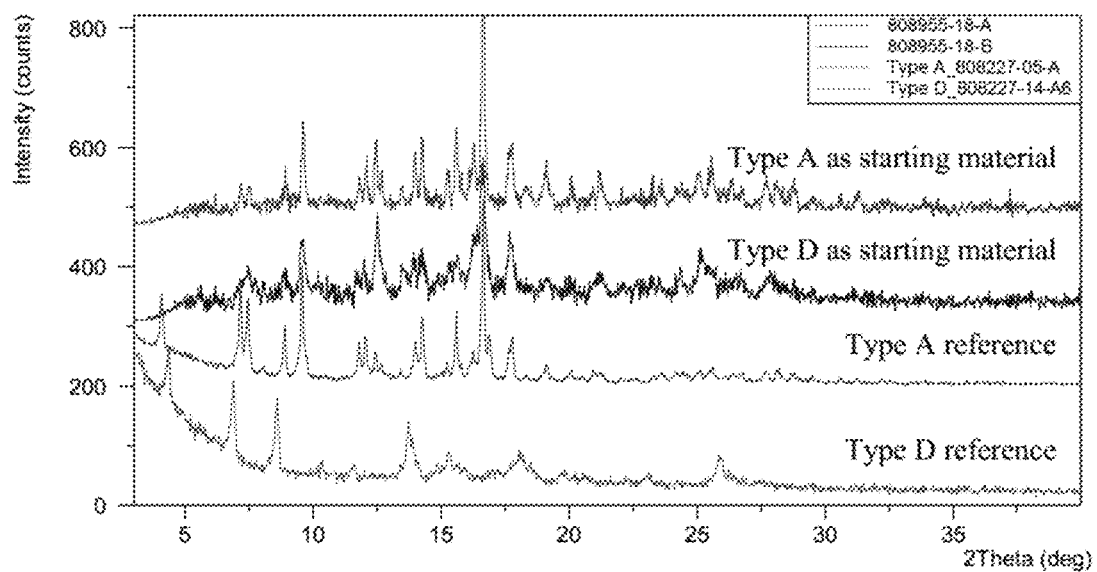
FIG. 18 shows an overlay of XRPD patterns of residual solid after solubility tests.

About 5 mg of each crystal type of solid (Form A of BBR-UDCA and Form D of BBR-UDCA, respectively) was weighed in separate 3-mL bottle, suspended into 1 mL of water, slurried (1000 rpm) at RT for 24 hours, and then centrifuged at 10000 rpm for 3 minutes. The resulting residual solids were characterized by XRPD and supernatant was measured by HPLC-DAD/ELSD. Due to the poor UV absorption of UDCA, DAD was used as the detector only for BBR and ELSD was used for both BBR and UDCA. As shown in FIG. 18, no matter the initial crystal types, the crystal type of both residual solids after solubility test was Form A, indicating that Form D converted to Form A during solubility experiment. With Form A as the starting material, the solubility of BBR was 0.35 mg/mL or 0.33 mg/mL using DAD or ELSD as detectors, respectively. The solubility of UDCA was 0.42 mg/mL, indicating the molar ratio was 0.94:1 (BBR:UDCA). With Form D as the starting material, the solubility of BBR was 0.42 mg/mL or 0.41 mg/mL using DAD or ELSD as detectors, respectively. The solubility of UDCA was 0.52 mg/mL, indicating the molar ratio was 0.93:1 (BBR:UDCA). The reason of the deviation from 1:1 may be that after HTD 1801 dissolving in water, a small amount of disproportionation occurred and it was hardly detected by XRPD due to its limited amount.

According to the results, Form D gave a better solubility in water than Form A.

TABLE 9

Summary of Solubility Evaluation

| Starting material | Form of residual solid | Solubility of BBR (mg/mL)* | Solubility of BBR (mg/mL)# | Solubility of UDCA (mg/mL)# |
|---|---|---|---|---|
| Type A | Type A | 0.35 | 0.33 | 0.42 |
| Type D | Type A | 0.42 | 0.41 | 0.52 |

*using DAD as detector;
using ELSD as detector.

Single Crystal Growth and Structure Analysis

Single crystals of compound HTD1801 hemi-nonahydrate were obtained by liquid vapor diffusion in ACN/H$_2$O (1:5, v:v)/MTBE mixture solvent system. The SCXRD characterization and structure analysis of the single crystal confirmed that it is in monoclinic crystal system and P21 space group. There are two BBR cations, two UDCA anions and nine H$_2$O molecules per asymmetric unit while each unit cell contains two asymmetric units, which means that there are four BBR cations, four UDCA anions and eighteen $H_2O$ molecules per unit cell. Adjacent UDCA anions and $H_2O$ molecules are connected to each other to form the 3-D supramolecular framework structure with 1-D linear channels by intermolecular hydrogen bonding (O—H . . . O) while the BBR cations are stacked orderly in the channels by 7C-7C interaction to form the 3-D crystal structure of the crystal eventually.

TABLE 10

Structural Information and Refinement Parameters for HTD1801 Hemi-nonahydrate Single Crystal

| | |
|---|---|
| Identification code | CP2276 |
| Empirical formula | $C_{44}H_{66}NO_{12.5}$ |
| Formula weight | 808.97 |
| Temperature | 153.15 K |
| Wavelength | Mo Kα (0.71073Å) |
| Crystal system, space group | Monoclinic, $P2_1$ |
| Unit cell dimensions | a = 23.5456(12)Å |
| | b = 7.4294(4) Å |
| | c = 25.3314(13)Å |
| | α = 90° |
| | β = 109.860(2)° |
| | γ = 90° |
| Volume | 4167.7(4)Å$^3$ |
| Z, Calculated density | 4, 1.289 g/cm$^3$ |
| Absorption coefficient | 0.093 mm$^{-1}$ |
| F(000) | 1748.0 |
| Crystal size | 0.1 × 0.025 × 0.01 mm |
| 2 Theta range for data collection | 4.826° to 55.266° |
| Limiting indices | −30 ≤ h ≤ 30 |
| | −9 ≤ k ≤ 9 |
| | −33 ≤ 1 ≤ 32 |
| Reflections collected/unique | 89416/19234 [R(int) = 0.2125] |
| Completeness | 99.00% |
| Refinement method | Full-matrix least-squares on F$^2$ |
| Data/restraints/parameters | 19234/19/1097 |
| Goodness-of-fit on F$^2$ | 1.006 |
| Final R indices [I > 2sigma(I)] | $R_1$ = 0.0881, $wR_2$ = 0.1238 |
| Largest diff. peak and hole | 0.28 and −0.30e · A$^{-3}$ |

The XRPD overlay (FIG. 12) showed that the XRPD pattern of Form A matched well with the XRPD pattern of the obtained single crystal. In addition, the TGA data of Form A showed that a weight loss of 9.4% was observed, while the theoretical weight loss of hemi-nonahydrate was 10.0%. All these results indicated that Form A was a hemi-nonahydrate of BBR-UDCA.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The above examples contain important additional information, exemplification and guidance that can be adapted to the practice of this invention in its various embodiments and equivalents thereof.

What is claimed is:

1. A solid form, which is Form A of berberine ursodeoxycholate, having an X-ray powder diffraction (XRPD) pattern comprising one or more peaks at 2θ values selected from the group consisting of: 7.06, 7.34, 8.79, 9.47, 11.94, 14.17, 15.50, 16.54 and 16.78° (±0.2°), wherein the Form A of berberine ursodeoxycholate has the formula:

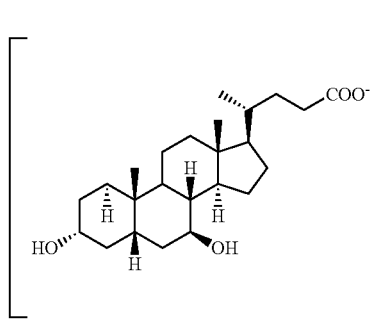

-continued

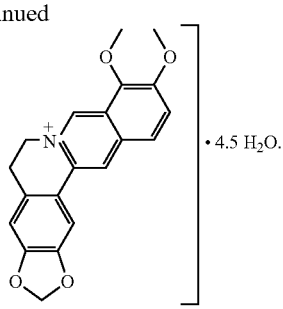

·4.5 H₂O.

2. The solid form of claim 1, having an X-ray powder diffraction (XRPD) pattern that further comprises one or more peaks at 2θ values of 3.98, 7.93, 11.70, 12.34, 12.55, 13.90, 15.14, 16.16, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49° (±0.2°).

3. The solid form of claim 1, having an X-ray powder diffraction (XRPD) pattern comprising peaks at 2θ values of 3.98, 7.06, 7.34, 7.93, 8.79, 9.47, 11.70, 11.94, 12.34, 12.55, 13.90, 14.17, 15.14, 15.50, 16.16, 16.54, 16.78, 17.53, 17.67, 18.23, 19.03, 19.98, 20.87, 21.13, 21.96, 23.49, 24.24, 24.97, 25.50, 26.63, 27.60, 28.06, 28.63, 29.40 and 30.49° (±0.2°).

4. The solid form of claim 1, wherein the solid form is a crystalline form.

5. The solid form of claim 4, wherein the crystalline form is characterized by a monoclinic crystal system and P2₁ space group.

6. The solid form of claim 4, wherein each unit cell contains two asymmetric units and there are two BBR cations, two UDCA anions and nine H₂O molecules per asymmetric unit, and four BBR cations, four UDCA anions and eighteen H₂O molecules per unit cell.

7. The solid form of claim 1, wherein the solid form has an X-ray powder diffraction (XRPD) pattern comprising peaks at diffraction angles 2θ essentially the same as the one presented in FIG. 1.

8. The solid form of claim 1, wherein the solid form is characterized by a purity of 70% or higher.

9. The solid form of claim 1, wherein the solid form is characterized by a purity of 95% or higher.

10. A pharmaceutical composition comprising the solid form of claim 1 and a pharmaceutically acceptable excipient, carrier, or diluent.

11. The pharmaceutical composition of claim 10, further comprising, in addition to berberine ursodeoxycholate, one or more other therapeutically effective agents.

12. The pharmaceutical composition of claim 10, further comprising one or more agents selected from the group consisting of vitamin D, vitamin C, vitamin E, vitamin B12, vitamin A, benfotiamine, chromium picolinate and vanadium.

13. The pharmaceutical composition of claim 10, further comprising one or more agents selected from the group consisting of omega-3 fatty acids, S-adenosylmethionine, N-acetyl cysteine, silymarin, polyenylphosphatidylcholine, and resveratrol.

14. A composition comprising Form A of berberine ursodeoxycholate according to claim 1.

15. A unit dosage form comprising a pharmaceutical composition according to claim 10.

* * * * *